US012683005B2

(12) United States Patent
O'Mahony et al.

(10) Patent No.: US 12,683,005 B2
(45) Date of Patent: Jul. 14, 2026

(54) TREATMENT PROFILES

(71) Applicant: GAMBRO LUNDIA AB, Lund (SE)

(72) Inventors: John O'Mahony, Maple Grove, MN (US); Andrew Wenger, Osseo, MN (US)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 17/874,808

(22) Filed: Jul. 27, 2022

(65) Prior Publication Data

US 2022/0367030 A1      Nov. 17, 2022

Related U.S. Application Data

(63) Continuation of application No. 17/321,013, filed on May 14, 2021, now Pat. No. 11,404,155, which is a continuation of application No. 14/652,228, filed as application No. PCT/US2013/075656 on Dec. 17, 2013, now abandoned.

(60) Provisional application No. 61/747,852, filed on Dec. 31, 2012.

(51) Int. Cl.
| | |
|---|---|
| *G06F 3/04842* | (2022.01) |
| *G06F 3/0482* | (2013.01) |
| *G16H 20/40* | (2018.01) |
| *G16H 40/63* | (2018.01) |

(52) U.S. Cl.
CPC ........... *G16H 20/40* (2018.01); *G06F 3/0482* (2013.01); *G06F 3/04842* (2013.01); *G16H 40/63* (2018.01)

(58) Field of Classification Search
None
See application file for complete search history.

(56) References Cited

U.S. PATENT DOCUMENTS

| | | | |
|---|---|---|---|
| 5,438,510 A | 8/1995 | Bryant | |
| 5,441,636 A | 8/1995 | Chevallet | |
| 5,679,245 A | * 10/1997 | Manica | A61M 1/3468 |
| | | | 210/143 |
| 5,762,805 A | 6/1998 | Truitt | |
| 5,776,345 A | 7/1998 | Truitt | |
| 5,910,252 A | 6/1999 | Truitt | |
| 6,146,523 A | 11/2000 | Kenley | |

(Continued)

FOREIGN PATENT DOCUMENTS

| | | |
|---|---|---|
| CN | 102215942 | 10/2011 |
| DE | 102010056605 A1 | 6/2012 |

(Continued)

OTHER PUBLICATIONS

Office Action issued in China for Application No. 201910418142.2 dated Nov. 29, 2022 (21 pages). English translation included.

(Continued)

*Primary Examiner* — Nhat Huy T Nguyen
(74) *Attorney, Agent, or Firm* — Mueting Raasch Group

(57)      ABSTRACT

Extracorporeal blood treatment systems and methods to use and modify/create treatment profiles for extracorporeal blood treatments. For example, treatment profiles may include one or more preset, or predefined, settings or values for an extracorporeal blood treatment such as, e.g., therapy type, therapy set (e.g., tubing set, filter set, etc.), anticoagulation type, and one or more flow rates, etc.

27 Claims, 18 Drawing Sheets

(56) References Cited

U.S. PATENT DOCUMENTS

| | | | | |
|---|---|---|---|---|
| 6,442,748 | B1 * | 8/2002 | Bowman-Amuah | ........................ |
| | | | | G06F 9/4493 |
| | | | | 707/999.009 |
| 7,303,540 | B2 | 12/2007 | O'Mahony | |
| 7,988,850 | B2 | 8/2011 | Roncadi | |
| 8,062,513 | B2 | 11/2011 | Yu | |
| 8,095,390 | B2 | 1/2012 | Bluemler | |
| 8,197,439 | B2 | 6/2012 | Wang | |
| 8,257,582 | B2 | 9/2012 | Yu | |
| 8,485,998 | B2 | 7/2013 | Moll | |
| 8,512,554 | B2 | 8/2013 | Yu | |
| 8,518,021 | B2 | 8/2013 | Stewart | |
| 8,560,510 | B2 | 10/2013 | Brueggerhoff | |
| 9,050,411 | B2 | 6/2015 | Kelly | |
| 9,241,958 | B2 * | 1/2016 | Smith | .................... A61K 33/42 |
| 9,675,745 | B2 | 6/2017 | Kelly | |
| 9,690,909 | B2 * | 6/2017 | Stewart | .................. G16H 70/40 |
| 2002/0022973 | A1 * | 2/2002 | Sun | ........................ G16H 40/67 |
| | | | | 705/3 |
| 2002/0029776 | A1 | 3/2002 | Blomquist | |
| 2005/0277911 | A1 | 12/2005 | Stewart | |
| 2008/0071210 | A1 * | 3/2008 | Moubayed | ............. G16H 40/63 |
| | | | | 604/67 |
| 2008/0072896 | A1 * | 3/2008 | Setzer | .................... G16Z 99/00 |
| | | | | 128/200.24 |
| 2008/0161751 | A1 | 7/2008 | Plahey | |
| 2008/0176210 | A1 | 7/2008 | Moll | |
| 2009/0113335 | A1 | 4/2009 | Sandoe | |
| 2010/0042035 | A1 | 2/2010 | Moissl | |
| 2010/0064257 | A1 | 3/2010 | Buck | |
| 2010/0121246 | A1 * | 5/2010 | Peters | .................. A61M 1/342 |
| | | | | 345/173 |

| | | | | |
|---|---|---|---|---|
| 2011/0004351 | A1 | 1/2011 | Kelly | |
| 2011/0066693 | A1 | 3/2011 | Basaglia | |
| 2011/0077586 | A1 | 3/2011 | Plahey | |
| 2011/0238032 | A1 * | 9/2011 | McTaggart | ............ G16H 20/17 |
| | | | | 700/282 |
| 2012/0022442 | A1 | 1/2012 | Yu | |
| 2012/0102010 | A1 | 4/2012 | Brueggerhoff | |
| 2013/0165847 | A1 | 6/2013 | Scarpaci | |
| 2013/0283030 | A1 * | 10/2013 | Drew | .................... G16H 40/63 |
| | | | | 713/100 |
| 2016/0022892 | A1 | 1/2016 | Eifler | |
| 2017/0274141 | A1 | 9/2017 | Stewart | |

FOREIGN PATENT DOCUMENTS

| | | | |
|---|---|---|---|
| EP | | 0668793 | 4/2000 |
| EP | | 1765436 | 6/2009 |
| EP | | 2314333 | 4/2011 |
| EP | | 2368588 | 9/2011 |
| EP | | 1938849 | 3/2013 |
| EP | | 2517742 | 5/2016 |
| EP | | 1936524 | 3/2018 |
| WO | WO 2004/053768 | | 6/2004 |
| WO | WO 2007/023329 | | 4/2011 |
| WO | WO 2014/184087 | | 11/2014 |

OTHER PUBLICATIONS

International Preliminary Report on Patentability for Application No. PCT/US2013/075656 dated Jul. 9, 2015 (9 pages).
International Search Report and Written Opinion for PCT/US2013/075656 dated Jun. 16, 2014 (12 pages).

* cited by examiner

TREATMENT PROFILES

CROSS-REFERENCE

This application is a continuation of U.S. application Ser. No. 17/321,013 filed May 14, 2021, and which is a U.S. application Ser. No. 14/652,228 filed Jun. 15, 2015, now abandoned, and which is a U.S. National Stage Application of International Application No. PCT/US2013/075656, filed Dec. 17, 2013 and published in English on Jul. 3, 2014, as International Publication No. WO 2014/105516 A1, which claims the benefit under 35 U.S.C. 119 (e) of U.S. Provisional Application Ser. No. 61/747,852, filed Dec. 31, 2012, all of which is are incorporated herein by reference in their entirety.

BACKGROUND

The disclosure herein relates to extracorporeal blood treatment. More particularly, the disclosure relates to user interfaces for the selection and/or modification of treatment profiles for extracorporeal blood treatment.

Many different settings and/or parameters are selected by a user, e.g., a clinician, when preparing an extracorporeal blood treatment for a patient. For example, the therapy type, anticoagulation type, therapy set (e.g., filter set, tubing set, etc.), etc. may be selected and/or configured by a clinician prior to the start of the treatment.

SUMMARY

The present disclosure describes systems and methods that provide for selection, creation, and/or modification of profiles for an extracorporeal blood treatment. Each profile may include a number of presets (e.g., preset settings, preset values, preset types, etc.) for one or more different settings for use in an extracorporeal blood treatment. When preparing an extracorporeal blood treatment system for treatment of a patient, a user may select a profile, and the system may be configured according to the selected profile. After a profile has been selected, a user may change or modify one or more of the preset settings before beginning the treatment. Additionally, the exemplary methods and systems described herein may allow a user to create and/or modify profiles for future use. Further exemplary methods and systems described herein may allow a user to copy one or more profiles between extracorporeal blood treatment systems.

One exemplary extracorporeal blood treatment system may include a display apparatus, input apparatus (e.g., a touch screen, etc.), and computing apparatus. The display apparatus may include a graphical user interface, where the graphical user interface is configured to depict a profile identifier region, a therapy type region, and a therapy set region. The input apparatus may be configured to allow a user to select a profile using the profile identifier region of the graphical user interface. The computing apparatus may be operatively coupled to the display apparatus and the input apparatus. The computing apparatus may be configured to store a plurality of profiles, where each profile of the plurality of profiles may include a preset therapy type of a plurality of different therapy types (e.g., SCUF, CVVH, CVVHD, CVVHDF, TPE, HP, MARS, and carbon dioxide removal) and a preset therapy set of a plurality of different therapy sets. The computing apparatus may be configured to allow a user to use the input apparatus to select a profile of the plurality of profiles using a profile identifier region of a graphical user interface and display on the graphical user interface the preset therapy type of the selected profile in a therapy type region and the preset therapy set of the selected profile in a therapy set region.

One exemplary method for an extracorporeal blood treatment system may include storing a plurality of profiles, where each profile of the plurality of profiles may include at least a preset therapy type of a plurality of different therapy types (e.g., SCUF, CVVH, CVVHD, CVVHDF, TPE, HP, MARS, and carbon dioxide removal) and a preset therapy set of a plurality of different therapy sets, providing a graphical user interface including a profile identifier region, a therapy type region, and a therapy set region, providing an input apparatus (e.g., a touch screen, etc.) configured to allow a user to select a profile of the plurality of profiles using the profile identifier region of the graphical user interface, allowing a user to use the input apparatus to select a profile of the plurality of profiles using the profile identifier region of the graphical user interface, and displaying on the graphical user interface the preset therapy type of the selected profile in the therapy type region and the preset therapy set of the selected profile in the therapy set region.

In one or more exemplary embodiments, each profile of the plurality of profiles may further include an identifier and the computing apparatus may be further configured to execute or the method may further include displaying the identifier of each of the plurality of profiles and allowing a user to use the input apparatus to select a profile of the plurality of profiles by selecting the identifier of the profile.

In one or more exemplary embodiments, the graphical user interface is further configured to depict a profile filter region and each profile of the plurality of profiles further includes identification data (e.g., prescribing doctor, weight, age, gender disease state, location, patient identifier, and intracellular volume). The computing apparatus may be further configured to execute or the method may further include allowing a user to use the input apparatus to select one or more filters using the profile filter region and displaying on the graphical user interface one or more profiles of the plurality of profiles based on the one or more selected filters.

In one or more exemplary embodiments, the computing apparatus is further configured to execute or the method may further include allowing a user to use the input apparatus to select at least one of a different therapy type of the plurality of different therapy types than the preset therapy type of the selected profile using the therapy type region of the graphical user interface and/or a different therapy set of the plurality of different therapy sets than the preset therapy set of the selected profile using the therapy set region of the graphical user interface.

In one or more exemplary embodiments, the computing apparatus is further configured to execute or the method may further include allowing a user to use the input apparatus, without selecting a profile of the plurality of profiles, to select at least one of a therapy type of the plurality of different therapy types using the therapy type region of the graphical user interface and a therapy set of the plurality of different therapy sets using the therapy set region of the graphical user interface.

In one or more exemplary embodiments, the graphical user interface may be further configured to depict an anticoagulation region and each profile of the plurality of profiles further may include a preset anticoagulation type of a plurality of different types of anticoagulation. The computing apparatus may be further configured to execute or the method may further include displaying on the graphical user interface the preset anticoagulation type of the selected profile in an anticoagulation region of the graphical user interface. In at least one embodiment, the computing apparatus may be further configured to execute or the method may further include allowing a user to use the input apparatus to select a different anticoagulation type of the plurality of different types of anticoagulation than the present anticoagulation type using the anticoagulation region of the graphical user interface.

In one or more exemplary embodiments, each profile of the plurality of profiles further may include a preset value for at least one flow rate of a plurality of flow rates and the graphical user interface may be further configured to depict a flow rate region. The computing apparatus may be further configured to execute or the method may further include displaying on the graphical user interface the preset value of the at least one flow rate of the selected profile in a flow rate region. In at least one embodiment, the computing apparatus may be further configured to execute or the method may include allowing a user to use the input apparatus to adjust the preset value of the at least one flow rate using flow rate region and displaying on the graphical user interface an indication proximate the adjusted preset value of the at least one flow rate in the flow rate region.

In one or more exemplary embodiments, each profile of the plurality of profiles may further include at least one preset alarm value for at least one alarm limit of a plurality of alarm limits and the graphical user interface may be further configured to depict an alarm region. The computing apparatus may be further configured to execute or the method may further include displaying the at least one preset alarm value for at least one alarm limit of the selected profile in an alarm region on the graphical user interface and allowing a user to use the input apparatus to adjust the at least one preset alarm value of the at least one alarm limit of the plurality of alarm limits of the selected profile using the alarm region of the graphical user interface.

In one or more exemplary embodiments, each profile of the plurality of profiles may further include at least one preset anticoagulation value for at least one anticoagulation advisory of a plurality of anticoagulation advisories and the graphical user interface may be configured to depict an anticoagulation advisory region. The computing apparatus may be further configured to execute or the method may further include displaying the at least one preset anticoagulation value for the at least one anticoagulation advisory of the plurality of anticoagulation advisories of the selected profile in an anticoagulation advisory region on the graphical user interface and allowing a user to use the input apparatus to adjust the at least one preset anticoagulation value of at least one anticoagulation advisory of the plurality of anticoagulation advisories of the selected profile using the anticoagulation advisory region of the graphical user interface.

One exemplary extracorporeal blood treatment system may include display apparatus, input apparatus, and computing apparatus. The display apparatus may include a graphical user interface, where the graphical user interface may be configured to depict a profile identifier region, a therapy type region, and a therapy set region. The input apparatus (e.g., a touch screen, etc.) may be configured to allow a user to create a profile identifier using the profile identifier region of the graphical user interface, to select a therapy type using the therapy type region of the graphical user interface, and to select a therapy set using the therapy set region of the graphical user interface. The computing apparatus may be operatively coupled to the display apparatus and the input apparatus and may be configured to store a plurality of profiles. Each profile of the plurality of profiles may include an identifier, at least a preset therapy type of a plurality of different therapy types (e.g., SCUF, CVVH, CVVHD, CVVHDF, TPE, HP, MARS, and carbon dioxide removal), and a preset therapy set of a plurality of different therapy sets. The computing apparatus may be further configured to display a profile identifier region, a therapy type region and a therapy set region on the graphical user interface and allow a user to use the input apparatus to enter an identifier for a new profile of the plurality of profiles using the profile identifier region, to select a therapy type of the plurality of different therapy types to be the preset therapy type of the new profile using the therapy type region of the graphical user interface, and to select a therapy set of the plurality of different therapy sets to be the preset therapy set of the new profile using the therapy set region of the graphical user interface. The computing apparatus may be further configured to allow a user to save the new profile into the plurality of stored profiles.

One exemplary method for an extracorporeal blood treatment system may include providing a graphical user interface that may include a profile identifier region, a therapy type region, and a therapy set region and providing an input apparatus (e.g., a touch screen, etc.) configured to allow a user to create or edit a profile identifier using the profile identifier region of the graphical user interface, to select a therapy type using the therapy type region of the graphical user interface, and to select a therapy set using the therapy set region of the graphical user interface. The exemplary method may further include storing a plurality of profiles, where each profile of the plurality of profiles may include an identifier, at least a preset therapy type of a plurality of different therapy types (e.g., SCUF, CVVH, CVVHD, CVVHDF, TPE, HP, MARS, and carbon dioxide removal), and a preset therapy set of a plurality of different therapy sets. The exemplary method may further include allowing a user to use the input apparatus to enter an identifier for a new profile of the plurality of profiles using the profile identifier region of the graphical user interface, to select a therapy type of the plurality of different therapy types to be the preset therapy type of the new profile using the therapy type region of the graphical user interface, and to select a therapy set of the plurality of different therapy sets to be the preset therapy set of the new profile using the therapy set region of the graphical user interface, and allowing a user to save the new profile into the plurality of stored profiles.

One exemplary extracorporeal blood treatment system may include display apparatus, input apparatus, and a computing apparatus. The display apparatus may include a graphical user interface, where the graphical user interface may be configured to depict a profile identifier region, a profile selection region, a therapy type region, and a therapy set region. The input apparatus (e.g., a touch screen, etc.) may be configured to allow a user to edit a profile identifier using the profile identifier region of the graphical user interface, to select a profile using the profile selection region, to select a therapy type using the therapy type region of the graphical user interface, and to select a therapy set using the therapy set region of the graphical user interface. The computing apparatus may be operatively coupled to the display apparatus and the input apparatus and may be configured to store a plurality of profiles. Each profile of the plurality of profiles may include an identifier, at least a preset therapy type of a plurality of different therapy types (e.g., SCUF, CVVH, CVVHD, CVVHDF, TPE, HP, MARS, and carbon dioxide removal), and a preset therapy set of a plurality of different therapy sets. The computing apparatus may be further configured to display a profile identifier region, a profile selection region, a therapy type region, and a therapy set region on the graphical user interface, allow a user to use the input apparatus to select a profile of the plurality of profiles using the profile selection region of the graphical user interface, display on the graphical user interface the identifier of the selected profile in the profile identifier region, the preset therapy type of the selected profile in the therapy type region, and the preset therapy set of the selected profile in the therapy set region, allow a user to use the input apparatus to modify at least one of the preset therapy type of the selected profile to a different therapy type of the plurality of different therapy types using the therapy type region of the graphical user interface and the preset therapy set of the selected profile to a different therapy set of the plurality of different therapy sets using the therapy set region of the graphical user interface, and allow a user to save the modified profile into the plurality of stored profiles.

One exemplary method for an extracorporeal blood treatment system may include providing a graphical user interface including a profile identifier region, a profile selection region, a therapy type region, and a therapy set region, providing an input apparatus (e.g., a touch screen, etc.) configured to allow a user to create or edit a profile identifier using the profile identifier region of the graphical user interface, to select a therapy type using the therapy type region of the graphical user interface, and to select a therapy set using the therapy set region of the graphical user interface. The exemplary method may further include storing a plurality of profiles, where each profile of the plurality of profiles may include an identifier, at least a preset therapy type of a plurality of different therapy types (e.g., SCUF, CVVH, CVVHD, CVVHDF, TPE, HP, MARS, and carbon dioxide removal), and a preset therapy set of a plurality of different therapy sets. The exemplary method may further include displaying a profile identifier region, a profile selection region, a therapy type region, and a therapy set region on the graphical user interface, allowing a user to use the input apparatus to select a profile of the plurality of profiles using the profile selection region of the graphical user interface, and displaying on the graphical user interface the identifier of the selected profile in the profile identifier region, the preset therapy type of the selected profile in the therapy region, and the preset therapy set of the selected profile in the therapy set region. The exemplary method may further include allowing a user to use the input apparatus to modify at least one of the preset therapy type of the selected profile to a different therapy type of the plurality of different therapy types using the therapy type region of the graphical user interface and the preset therapy set of the selected profile to a different therapy set of the plurality of different therapy sets using the therapy set region of the graphical user interface and allowing a user to save the modified profile into the plurality of stored profiles.

In one or more embodiments, the graphical user interface may be further configured to depict an anticoagulation region, and each profile of the plurality of profiles may further include a preset anticoagulation type of a plurality of different types of anticoagulation. The computing apparatus may be further configured to execute or the method may further include displaying an anticoagulation region on the graphical user interface and allowing a user to use the input apparatus to select an anticoagulation type to be the preset anticoagulation type of the new or the selected profile using the anticoagulation region of the graphical user interface. In at least one embodiment, the computing apparatus may be further configured to execute or the method may further include allowing a user to use the input apparatus to modify the identifier of the new or the selected profile using the profile identifier region. In at least one embodiment, the computing apparatus may be further configured to execute or the method may further include allowing a user to save the new profile or the modified profile into the plurality of stored profiles if at least a therapy type and a therapy set has been selected.

In one or more embodiments, each profile of the plurality of profiles may further include a preset value for at least one flow rate of a plurality of flow rates, and the graphical user interface may be further configured to depict a flow rate region. The computing apparatus may be further configured to execute or the method may further include displaying a flow rate region on the graphical user interface and allowing a user to use the input apparatus to adjust the preset value of the at least one flow rate of the new or the selected profile using the flow rate region of the graphical user interface. In at least one embodiment, the computing apparatus may be further configured to execute or the method may further include displaying on the graphical user interface an indication proximate the adjusted preset value of the at least one flow rate in the flow rate region.

In one or more embodiments, each profile of the plurality of profiles may further include at least one preset alarm value for at least one alarm limit of a plurality of alarm limits, and the graphical user interface may be further configured to depict an alarm region. The computing apparatus may be further configured to execute or the method may further include displaying an alarm region on the graphical user interface and allowing a user to use the input apparatus to adjust at least one preset alarm value of the plurality of alarm limits of the new or the selected profile using the alarm region of the graphical user interface.

In one or more embodiments, each profile of the plurality of profiles may further include at least one preset anticoagulation value for at least one anticoagulation advisory of a plurality of anticoagulation advisories, and the graphical user interface may be further configured to depict an anticoagulation advisory region. The computing apparatus may be further configured to execute or the method may further include displaying an anticoagulation advisory region on the graphical user interface and an allowing a user to use the input apparatus to adjust at least one preset anticoagulation value of the plurality anticoagulation advisories of the new or the selected profile using the anticoagulation advisory region of the graphical user interface.

In one or more embodiments, the computing apparatus may be further configured to execute or the method may further include allowing a user to use the input apparatus to transfer at least one profile of the plurality of profiles to an external device. In one or more embodiments, the graphical user interface may be further configured to depict a profile selection region that may include a list of the identifiers of the plurality of profiles, and the computing apparatus may be further configured to execute or the method may further include displaying a profile selection region on the graphical user interface and allowing a user to use the input apparatus to select a profile of the plurality of profiles using the profile selection region of the graphical user interface. In at least one embodiment, the plurality of profiles may include at least one protected profile, and at least one of the identifier, preset therapy type, and preset therapy set of the at least one protected profile may not be modifiable by a user.

One exemplary extracorporeal blood treatment system may include display apparatus, input apparatus, and computing apparatus. The display apparatus may include a graphical user interface, where the graphical user interface may be configured to depict a profile selection interface and a profile creation/modification interface. The input apparatus may be configured to allow a user to select, create, and modify one or more profiles. The computing apparatus may be operatively coupled to the display apparatus and the input apparatus, and may be configured to store a plurality of profiles, where each profile of the plurality of profiles may include an identifier, at least a preset therapy type of a plurality of different therapy types, and a preset therapy set of a plurality of different therapy sets. The computing apparatus may be further configured to display on the graphical user interface a profile selection interface configured to allow a user to select a profile for use in a treatment and display on the graphical user interface a profile creation/modification interface configured to allow a user to modify one or more profiles of the plurality of profiles and/or to allow a user to create one or more profiles to be stored in the plurality of profiles. In at least one embodiment, the profile selection interface and the profile creation/modification interface may not be displayed at the same time.

One exemplary method for an extracorporeal blood treatment system may include providing a graphical user interface, where the graphical user interface may be configured to depict a profile selection interface and a profile creation/modification interface, providing an input apparatus configured to allow a user to select, create, and modify one or more profiles, and storing a plurality of profiles, where each profile of the plurality of profiles may include an identifier, at least a preset therapy type of a plurality of different therapy types, and a preset therapy set of a plurality of different therapy sets. The exemplary method may further include displaying on the graphical user interface a profile selection interface configured to allow a user to select a profile for use in a treatment and displaying on the graphical user interface a profile creation/modification interface configured to allow a user to modify one or more profiles of the plurality of profiles and/or to allow a user to create one or more profiles to be stored in the plurality of profiles. In at least one embodiment, the profile selection interface and the profile creation/modification interface may not be displayed at the same time.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
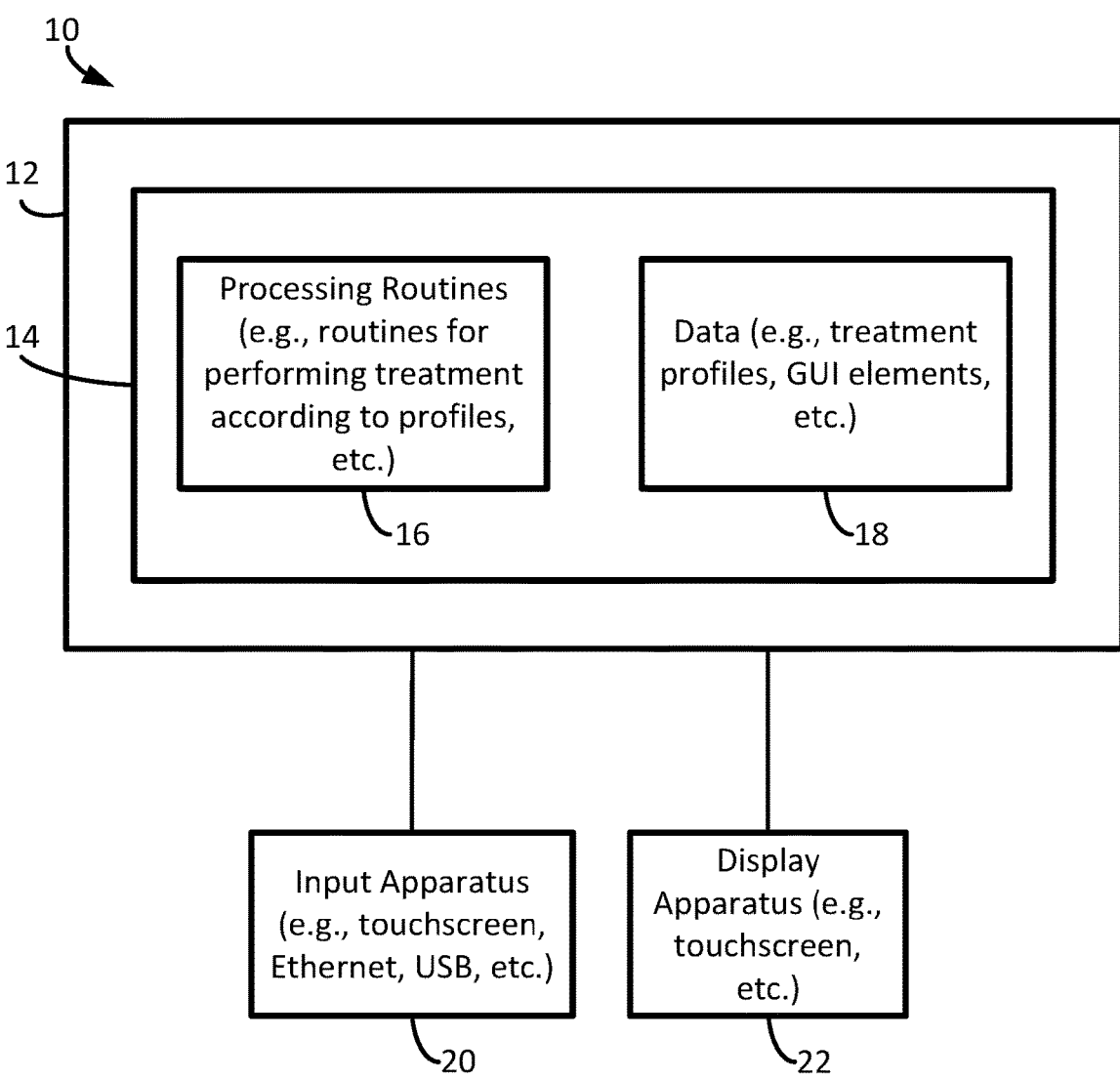
FIG. 1 is a block diagram of an exemplary extracorporeal blood treatment system including input apparatus and display apparatus that may utilize the user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods of selecting, modifying, and creating treatment profiles for use in an extracorporeal blood treatment shall be described with reference to FIGS. 1-18. As used herein, a treatment profile, or a profile for short, may be defined as a set of preset, or predefined, settings and values for an extracorporeal blood treatment. A profile may include one or more of the following: an identifier, a preset therapy type, a preset therapy set (e.g., including filter set, tubing set, etc.), a preset anticoagulation type, one or more preset flow rates, one or more preset alarm limits, one or more preset anticoagulation values, a patient identifier (e.g., ID), one or more replacement solutions, one or more dialysis solutions, etc. The exemplary systems and methods may provide, or allow a user to create, a plurality of different treatment profiles, each including at least one different setting or value from the next. When initiating, or preparing, an extracorporeal blood treatment, a user may select a profile and the preset settings of the selected profile may be loaded into the extracorporeal blood treatment system, which may expedite the setup process and also limit errors, e.g., input errors, etc.

An exemplary extracorporeal blood treatment system 10 depicted in FIG. 1 may be used to execute the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 that may be employed to carry out exemplary methods and/or processes for use in setting up (e.g., preparing for, configuring the system for, etc.) and performing extracorporeal blood treatment. For example, the computing apparatus 12 may be configured to allow a user to select a treatment profile using the input apparatus 20 (e.g., based on input from the user) and display apparatus 22 to configure, or set up, the system 10 to perform extracorporeal blood treatment according to the selected treatment profile (e.g., which will be described further herein with respect to FIGS. 4-12). Further, for example, the computing apparatus 12 may be configured to allow a user to create and/or modify one or more treatment profiles using the input apparatus 20 and display apparatus 22 (e.g., which will be described further herein with respect to FIGS. 13-18). Still further, for example, the computing apparatus 12 may be configured to allow a user to save a profile that includes a patient identifier, or ID, to another system or external device for later retrieval (e.g., when an entered patient identifier matches that of the saved profile).

The computing apparatus 12 may be operatively coupled to the input apparatus 20 and the display apparatus 22 to, e.g., transmit data to and from each of the input apparatus 20 and the display apparatus 22. For example, the computing apparatus 12 may be electrically coupled to each of the input apparatus 20 and the display apparatus 22 using, e.g., analog electrical connections, digital electrical connections, wireless connections, bus-based connections, etc. As described further herein, a user may provide input to the input apparatus 20 to manipulate, or modify, one or more graphical depictions displayed on the display apparatus 22 to select, create, and/or modify treatment profiles that may be used to configure the extracorporeal blood treatment system 10.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20 and display apparatus 22. The input apparatus 20 may include any apparatus capable of providing input to the computing apparatus 12 to perform the functionality, methods, and/or logic described herein. For example, the input apparatus 20 may include a touchscreen (e.g., capacitive touchscreen, a resistive touchscreen, a multi-touch touchscreen, etc.), a mouse, a keyboard, a keypad, a trackball, etc. The input apparatus 20 may allow a user to select, modify, and/or create profiles when used in conjunction with the display apparatus 22 (e.g., displaying a graphical user interface).

Likewise, the display apparatus 22 may include any apparatus capable of displaying information to a user, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more regions and areas used to select, modify, and/or create treatment profiles to be used in an extracorporeal blood treatment. For example, the graphical user interface displayed by the display apparatus 22 may include, or display, a profile region, a therapy type region, a therapy set region, a flow rate region, an alarm region, an anticoagulation region, etc. Each of these regions may be used by a user to view and/or modify a portion of the treatment profile being displayed on the graphical user interface of the display apparatus 22. As used herein, a "region" of a graphical user interface may be defined as a portion of the graphical user interface within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located with a region that is smaller than the region it is located within.

The processing programs or routines 16 may include programs or routines for performing computational mathematics, matrix mathematics, standardization algorithms, comparison algorithms, or any other processing required to implement one or more exemplary methods and/or processes described herein. Data 18 may include, for example, treatment data, profile identification data, profiles, profile data (e.g., preset values and/or settings), user accounts, anticoagulation sample periods, input/output sample periods, treatment durations, fluid flows, blood flows, patient identifiers, fluid periodic rates, solution identifiers, target blood temperature, CRCs, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion. In at least one embodiment, output information may include one or more profiles that may be saved on a server.

The program used to implement the methods and/or processes described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and when executed by a processor operable to perform operations such as the methods, processes, and/or functionality described herein.

Likewise, the system 10 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data). Additionally, the system 10 may be configured by one or more servers.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory such as NVRAM or FLASH, a CD-ROM, a punch card, magnetic recordable tape, etc.) containing digital bits (e.g., encoded in binary, trinary, etc.) that may be readable and/or writeable by computing apparatus 12 described herein. In at least one embodiment, the digital file may be transferred from a server and stored in random access memory (RAM).

Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that graphical user interfaces may be used in conjunction with the embodiments described herein. The graphical user interfaces may provide various features allowing for user input thereto, change of input, importation or exportation of files, or any other features that may be generally suitable for use with the processes described herein. For example, the graphical user interfaces may allow default values to be used or may require entry of certain values, limits, threshold values, or other pertinent information.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, microcontrollers, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The exemplary systems, and exemplary methods performed, or used, by such exemplary systems, described herein for the selection, creation, and/or modification of treatment profiles for use in extracorporeal blood treatments may be generally referred to as dialysis systems. The general terms extracorporeal treatment and dialysis as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE, which may technically be a pheresis procedure) shall be described herein with reference to the exemplary extracorporeal blood treatment system of FIGS. 2-3, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular fluid processing system.

Figure 2:
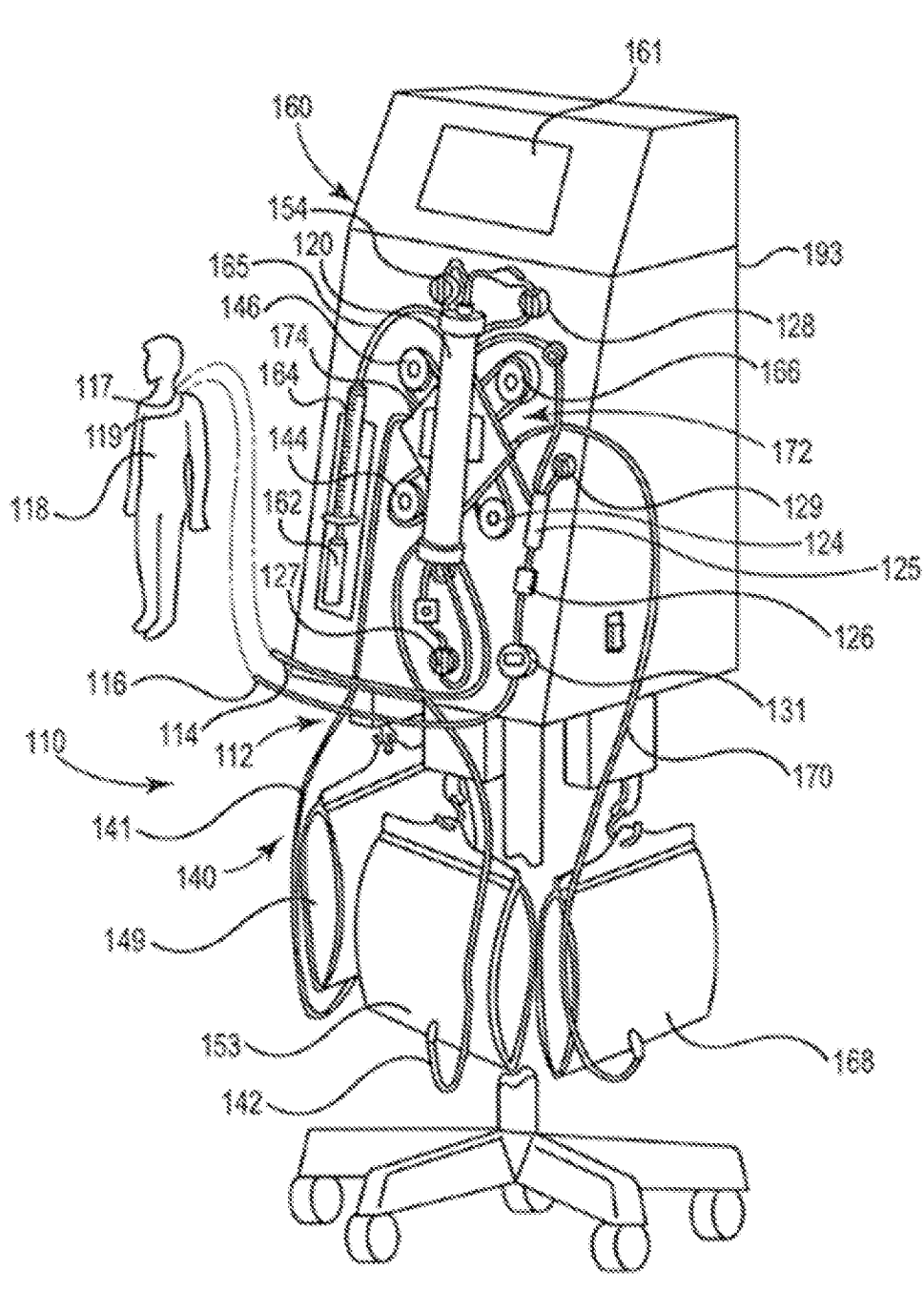
FIG. 2 is a perspective illustration of an exemplary fluid processing system that may include a graphical user interface as described herein.
Figure 3:
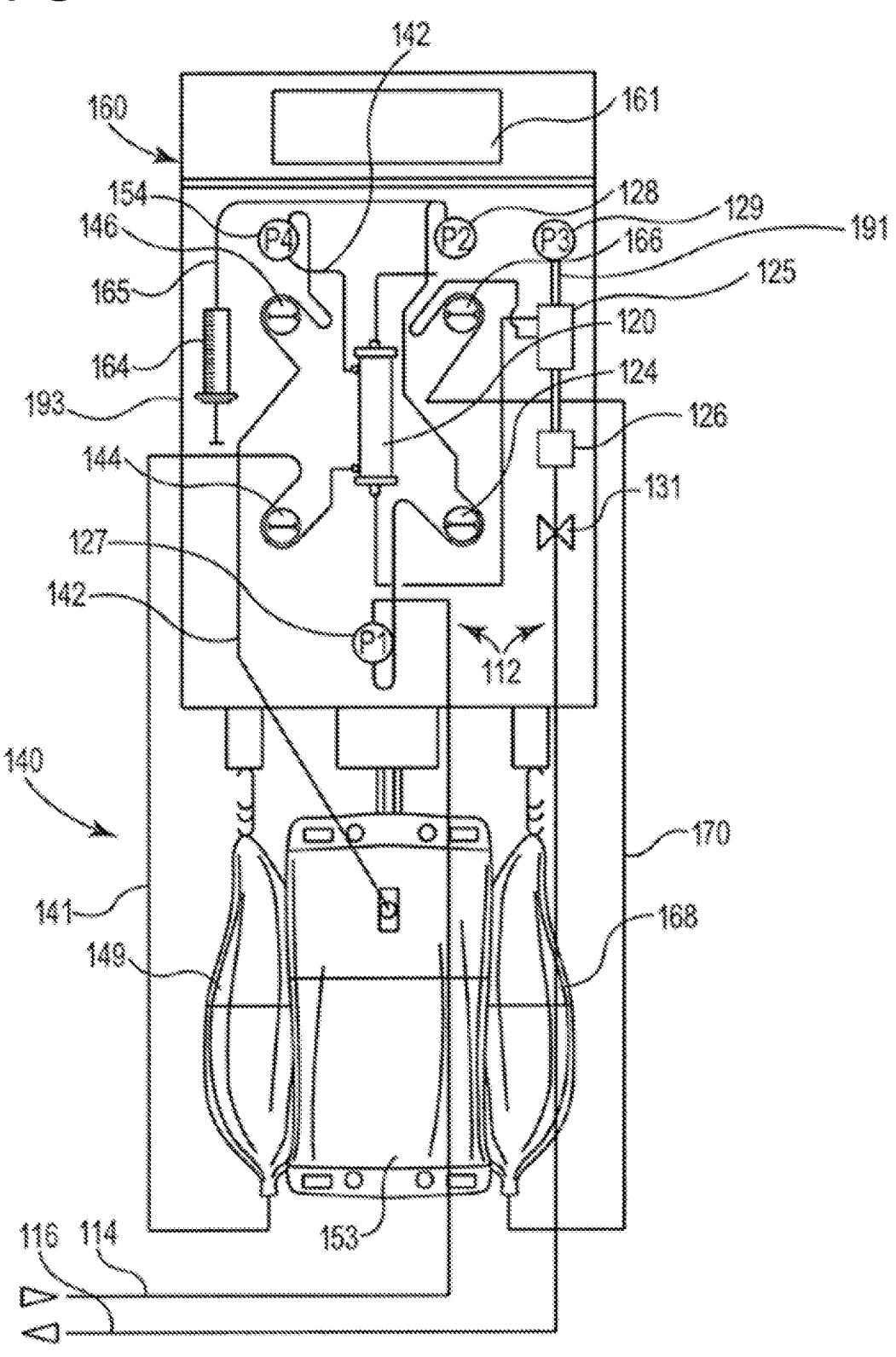
FIG. 3 is a front view of a portion of the exemplary fluid processing system shown in FIG. 2.

In the perspective and partial front views of FIGS. 2-3, the exemplary extracorporeal blood treatment system 110 that may use the graphical user interfaces as described herein generally includes a blood tubing circuit 112 having first and second tubing segments 114 and 116 which are both connected to the vascular system of a patient 118 via access and return devices 117 and 119, respectively. Devices 117 and 119 may be cannulas, catheters, winged needles or the like as would be understood by one skilled in the art. Tubing segments 114 and 116 are also connected to a filtration or processing unit 120. In dialysis, filtration unit 120 is a dialyzer, which is also often referred to as a filter. In TPE, it may also be referred to as a plasma filter. In this exemplary system 110, a peristaltic pump 124 is disposed in operative association with the first tubing segment 114. Numerous other component devices of blood circuit 112 are also included as, for example, pressure sensors 127, 128.

Also shown in FIGS. 2-3 is the processing fluid or filtrate side of system 110 which generally includes a processing fluid circuit 140 having first and second processing fluid tubing segments 141 and 142. Each of these tubing segments is connected to the filtration unit 120. In these FIGS. 2-3, a respective fluid pump 144, 146 is operatively associated with each of these tubing segments 141 and 142. First tubing segment 141 is also connected to a processing fluid source (e.g., fluid bag 149), which may include electrolytes premixed therein. Second tubing segment 142 is connected to a waste collection device (e.g., a waste container such as a bag 153). A pressure sensor 154 may also be disposed in second dialysis fluid tubing segment 142.

FIGS. 2-3 show a system that is common as a basic model for numerous dialysis procedures including TPE. Additional fluid lines, circuits, and components may be added (or deleted) to increase therapy options. Further, as shown in FIGS. 2-3, the system 110 includes an extracorporeal blood control apparatus 160 that provides numerous treatment options, which may be controlled and/or monitored via the control/display screen 161 (e.g., a control apparatus or controller provided in a system housing 193). Touch-screen controls may be incorporated herewith and/or other conventional knobs or buttons (not shown) may be used (e.g., graphical user interfaces may be displayed via a touchscreen as described herein). Other and more detailed information regarding an example apparatus 160 may be found in U.S. Pat. Nos. 5,679,245; 5,762,805; 5,776,345; and 5,910,252; inter alia.

A general dialysis treatment procedure as performed, for example, with an apparatus described with reference to FIGS. 2-3 will be generally described for exemplary purposes. First, blood is removed from the patient 118 via access device 117 and flows through access line 114 to the filter 120. Filter 120 processes this blood according to a selected one or more of a number of extracorporeal blood treatment profiles (e.g., selected and controlled via screen interface 161 of control apparatus 160) and then returns the processed or treated blood to the patient 118 through return line 116 and return device 119 inserted in or otherwise connected to the vascular system of the patient 118. The blood flow path to and from the patient 118, which includes the access device 117, the access line 114, the filter 120, as well as the return line 116 and return device 119 back to the patient, forms the blood flow circuit 112.

Pressure sensors may be used to sense various pressures in the system 110. For example, the pressure sensor 127 may be connected in the access line 114 and allow the fluid pressure in the access line 114 to be monitored and the second pressure sensor 128 may be connected in the blood circuit 112 between the first pump 124 and the blood entrance into the filter 120 and may be used to detect and monitor the pressure of the blood supplied to the entrance of the filter 120.

The system 110 may further include a deaeration chamber 125 in the return line to provide a conveyance path that operates like a vortex to propel air out of the blood. Post-filter replacement solution may be added into the deaeration chamber on the top of the blood to prevent an air/blood interface. A deaeration chamber monitor line 191 may connect the deaeration chamber 125 to an internal pressure transducer within the system housing 193 using a connection apparatus, such as, for example, a return pressure port 129. This enables return pressure monitoring, and removal of air from the deaeration chamber, if needed. A return clamp 131 connected in the blood circuit 112 selectively allows or terminates the flow of blood through the blood circuit 112 (e.g., return clamp 131 may be activated whenever air is detected in the blood by bubble detector 126). Further, a pump 162 may be connected to an anticoagulant container 164 to deliver anticoagulant through an anticoagulant line 165 to the blood in tubing segment 114 and a pump 166 may deliver replacement fluid from a replacement fluid container or bag 168 through a replacement fluid line 170.

The secondary flow circuit 140 is also shown in FIGS. 2-3 as it interacts with filter 120. The secondary flow circuit 140 is connected to the secondary chamber of filter 120. Matter extracorporeally removed from the blood is removed from the secondary chamber of filter 120 through the outlet tubing segment 142 of the secondary flow circuit 140, and matter extracorporeally added to the blood is moved into filter 120 through inlet tubing segment 141 of the secondary flow circuit 140. The secondary flow circuit 140 generally includes the fluid source such as bag 149, inlet fluid line 141, third peristaltic pump 144, the secondary chamber of the filter 120, a waste fluid line 142, pressure sensor 154, fourth pump 146, and the waste collection device such as container 153. The source fluid bag 149 may contain a sterile processing fluid, generally isotonic to blood, into which blood impurities will diffuse through the semi-permeable membrane of the filtration unit 120. The pump 144 is connected in inlet fluid line 141 for delivering processing fluid from the processing fluid source 149 into an entrance to the filter 120. The waste collection container 153 is provided to collect or receive matter from the blood transferred across the semi-permeable membrane in filter 120 and/or to receive the used processing fluid after it has passed through the filter 120. The fourth pump 146 is connected to the waste collection line 142 for moving body fluid from the filter 120 into the waste collection container 153. The pressure sensor 154 may also be located in the waste collection line 142 for the purpose of monitoring the pressure in the secondary chamber of filter 120. Further, although not shown, additional pumps may be included in the system 110 to pump materials for such as, e.g., calcium solutions, predilutions, etc.

The filtration unit 120, the flow tubing lines, and the other components in the primary and secondary flow circuits 112 and 140 described herein (with the exception, for example, of the pumps and perhaps a few other items) may be formed as an integral, replaceable unit (e.g., an extracorporeal blood set). This integral replacement unit may be referred to herein as a "therapy set." An example of such a therapy set, or integral replaceable unit, is described in greater detail in U.S. Pat. No. 5,441,636 entitled Integrated Blood Treatment Fluid Module (see also, U.S. Pat. No. 5,679,245, entitled Retention Device for Extracorporeal Treatment Apparatus). Any number of therapy sets for use in performing different therapies may be available depending on the system configuration.

As can generally be appreciated from FIGS. 2-3, the integrated tubing and filter module (identified by the reference numeral 172) includes the filter 120 and all the tubing and related components described above which are connectable to apparatus 160. For example, the filter and tubing may be retained on a plastic support member 174 which is, in turn, connectable to apparatus 160 (e.g., connectable to the system housing 193 of the apparatus 160). When in the operative position connected to apparatus 160, flexible fluid conducting tubing lines to and from the filtration unit 120 are held in operative, pump communicative loops for operative contact with the peristaltic pumping members of the pumps 124, 144, 146 and 166 to cause the fluid to flow through the primary (blood) and secondary (processing fluid) circuits 112 and 140. Module 172, including filter 120 and all the tubing lines and associated flow components may be disposable after use. The peristaltic pumping members of pumps 124, 144, 146, and 166 may be fixedly disposed on apparatus 160 (without the disposable tubing loop components) and may be re-usable. In general, electrical, mechanical, or electromechanical components are also fixedly disposed in or on apparatus 160 (e.g., connectable to the system housing 193 of the apparatus 160). Examples of such components include the display screen 161 (e.g., a touchscreen), the bubble detector 126, line clamps 131 and connection apparatus for coupling to pressure sensor apparatus used to implement pressure sensors 127, 128, 154.

Screenshots depicting exemplary graphical user interfaces for use in selecting and modifying one or more treatment profiles are depicted in FIGS. 4-12. Such exemplary graphical user interfaces may be depicted by the display apparatus 22 of the system 10 described herein with reference to FIG. 1 and/or the display screen 161 of FIGS. 2-3. Additionally, the graphical user interfaces described herein may be depicted on a touchscreen, and in such configuration, the input apparatus would also be the touchscreen.

Figure 4:
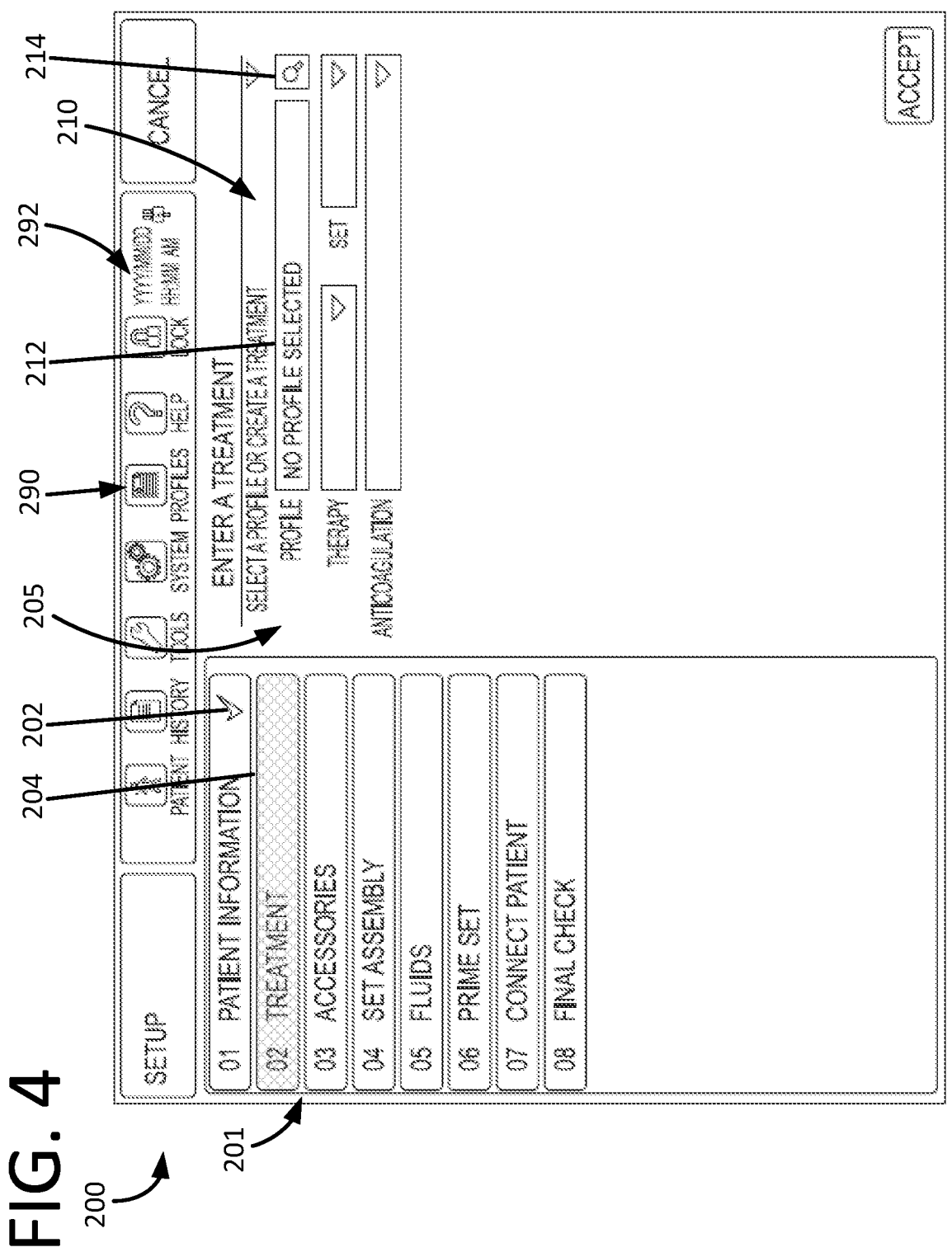
FIGS. 4-12 are screenshots of graphical user interfaces for use in selecting and/or modifying treatment profiles in extracorporeal blood treatment systems, for example, such as shown generally in FIGS. 1-3.

An exemplary graphical user interface 200 is depicted in FIG. 4 that may be generally used in the setup, or preparation, of an extracorporeal blood treatment. The graphical user interface 200 may include a step region 201 and a profile region 205. As shown, the step region 201 is depicted on the left side of the graphical user interface 200 and the profile region 205 is depicted on the right side of the graphical user interface 200. The step region 201 may include, or graphically depict, the various steps, or processes, used to prepare an extracorporeal blood treatment system for an extracorporeal blood treatment of a patient. As shown, the step region 201 includes exemplary steps: "01 Patient Information," "02 Treatment," "03 Accessories," "04 Set Assembly," "05 Fluids," "06 Prime Set," "07 Connect Patient," and "08 Final Check." When a step has been completed, a checkmark 202 may appear next to the title of the step in the step region 201. Further, the step that is presently being executed may be highlighted. As shown in FIG. 4, the "02 Treatment" step is currently being executed, and as such, is highlighted 204.

In the "02 Treatment" step, a user may be allowed to use the input apparatus (e.g., a touchscreen which may also be the display apparatus) to select a profile and modify a profile in the profile region 205. For example, a user may use the input apparatus to select a profile using a profile identifier region 210 of the graphical user interface 200. As shown, no profile is presently selected as indicated by the wording "No Profile Selected" located in an identifier area 212 of the profile identifier region 210. To the left of the identifier area 212 of the profile identifier region 210 is the wording "Profile" to indicate, for example, that this region is the profile identifier region 210.

Additionally, a user may not want to select a profile or may not find a profile that is suitable to be used. In this situation, no profile is selected using the profile identifier region 210 and the user may utilize the remainder of the profile region 205 of the graphical user interface 200 to configure the extracorporeal blood treatment system for a blood treatment. When no profile as been selected, the wording "No Profile Selected" may be displayed in the identifier area 212 of the profile identifier region 210. Further, as shown in FIG. 4, when a profile is selected, but one or more parameters and/or settings of the selected profile are modified, the name of the selected profile may still appear in the identifier area 212 but the wording "—Modified" may appear next to the name of the profile in the profile identifier area 212 to indicate that the identified profile has been modified.

Figure 5:
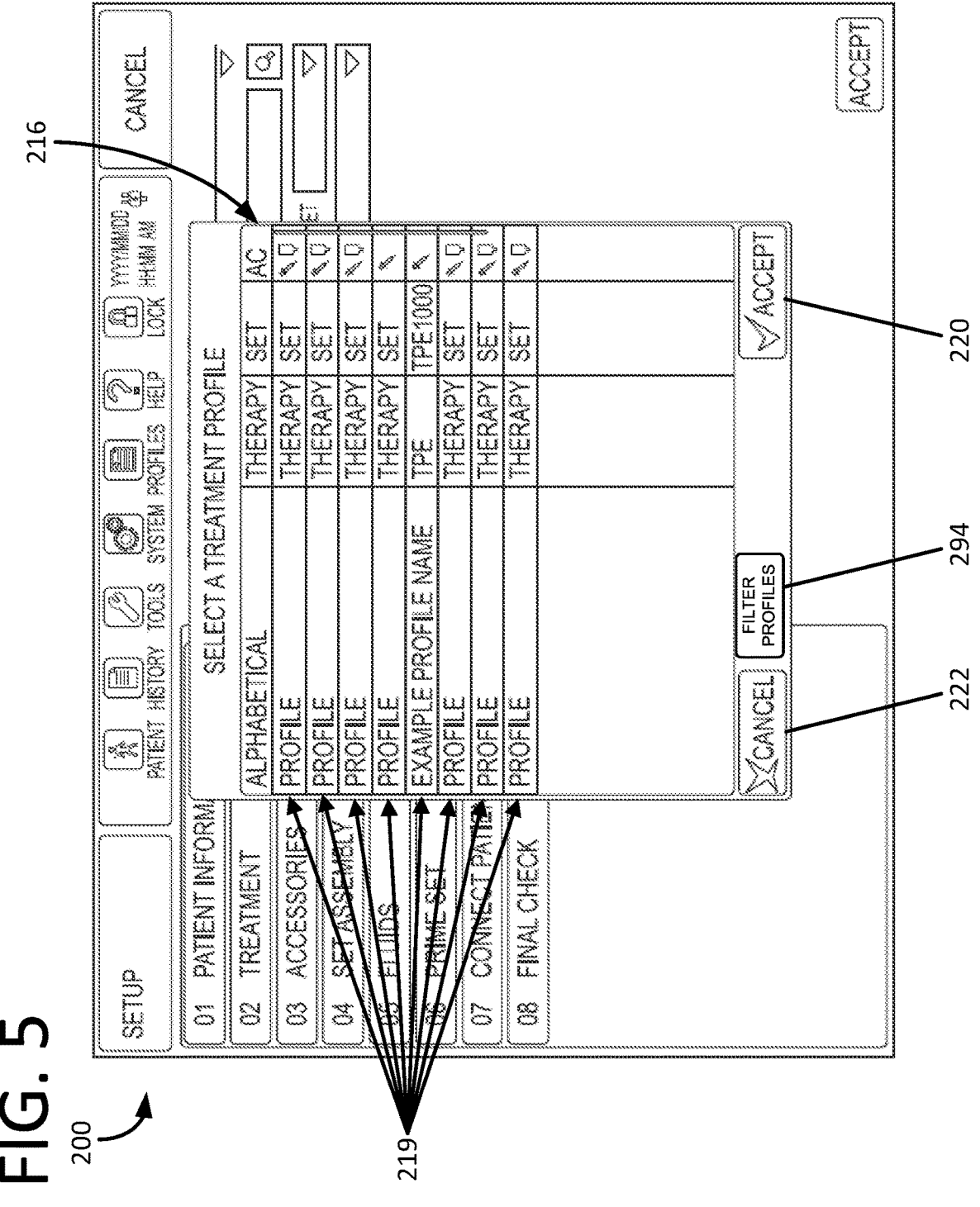

As described herein, a user may be allowed to use an input apparatus to select a profile using the profile identifier region 210. For example, a user may select a selection area 214 of the profile identifier region 210 that may result in the display of a profile selection region 216 including a list of selectable profiles 219 from a plurality of available profiles for use in extracorporeal blood treatment as shown in FIG. 5. As used herein, when a user "selects" a region or area of the graphical user interface, it is to be understood that selecting the region or area may be conducted in many different ways using many different types of input apparatus. For example, when the input apparatus is a touch screen, a user may select a region or area by "touching" the region or area with their finger or using a pointing device such as a stylus. Further, for example, when the input apparatus is a mouse or similar pointing device, a user may select a region or area by locating an arrow or cursor over the desired region or area and "clicking" the region or area. Still further, for example, when the input apparatus is a series of buttons and/or knobs, a user may select a region or area by using the buttons and/or knobs to navigate to the region or area and selecting it by depressing a button and/or knob.

As shown, the profile selection region 216 may be a "pop-over" window (e.g., a graphical element that is located over the remainder of the graphical user interface 200, which may be "grayed out" as non-functional until a profile has been selected or the profile selection process cancelled). The profile selection region 216 may list the plurality of available, selectable profiles 219 by the name, or identifier, of the plurality of profiles 219. The identifiers of the profiles 219 may be listed alphanumerically. Further, the therapy type and the therapy set for each profile may also be listed adjacent the identifier of each profile located in the same row as each profile identifier. Still further, the profile selection region 216 may include graphical elements, or icons, located in the same row as each profile to indicate what type of anticoagulation that each profile may include, or to indicate any other parameter or characteristic of the profile.

A user may select a profile by selecting the identifier, or name, of the profile, or any other item located in the same row as the name of the profile, and subsequently select the accept area, or button, 220 located in the lower right-hand corner of the profile selection region 216 to accept the selected profile and dismiss (e.g., make disappear) the profile selection region 216. Additionally, if a user does not desire to select a profile (e.g., if a user does not see a profile that they want to select), the user may select the cancel area, or button, 222. Further, the profiles 219 displayed in the profile selection region 216 may be sorted by selecting the following column headers: "Alphabetical," which will sort the profiles alphabetically from top to bottom, "Therapy" that will sort the profiles by therapy type, "Set" that will sort the profiles by therapy set," and "AC" that will sort the profiles by anticoagulation type.

If a system includes many treatment profiles, the profiles may be difficult to look, or browse, through to find a user desired profile. As such, the exemplary graphical user interface 200 may include a profile filter to, e.g., limit the amount of profiles displayed to a user in the profile selection region 216. To initiate the profile filter, a user may select the "Filter Profiles" area, or button, 294 located within the profile selection region 216 that may display a profile filter region including one or more filters, e.g., characteristics or parameters of profiles by which the profiles may be filtered. For example, each profile may further include identification data. Such identification data may include one or more of prescribing doctor, weight, age, gender disease state, location, intracellular volume, patient identifier (ID), body surface area, room numbers, validity period, etc.

The profile filter region may allow a user to filter the profiles by using the identification data (e.g., patient identifier, prescribing doctor, etc.) of the profiles. For instance, a user may want to only display profiles for a particular prescribing doctor, and as such, use the profile filter region to select a particular prescribing doctor. After selecting a particular doctor in the profile filter region, only the profiles that include the identification data that has the prescribing doctor may be displayed in the profile selection region 216. In at least one embodiment, instead of filtering out the unwanted profiles, the profile selection region 216 may sort the profiles by the selected filter. For instance, if a user selects "prescribing doctor" in the profile filter region, the profile selection region 216 may display the profiles arranged by prescribing doctor.

In at least one embodiment, a patient identifier may be entered, or input, (e.g., using a bar code reader) into the system and a relevant profile may be selected based on the entered patient identifier. For example, a patient identifier may correspond to at least one profile (e.g., be included in the profile), and thus when the patient identifier is inputted, the at least one profile corresponding the patient identifier may be selected.

Further, one or more profiles listed in the profile selection region 216 may be unable to be used, or unacceptable for use, in the extracorporeal blood treatment system due to, e.g., a conflict between the solutions, therapy sets, antico- agulation types, etc. available for use. As such, the one or more profiles that are unacceptable for use may be "greyed out" in the profile selection region 216 or not available, or shown, in the profile selection region 216.

Although a profile selection region 216 is described and shown herein to be used to select a profile, other embodi- ments may use other processes and/or graphical elements to allow a user to select a profile. For example, a "pull down" menu may be presented and used for profile selection. Further, for example, a "pop-up" window or a new screen may be presented and used for profile selection.

Figure 6:
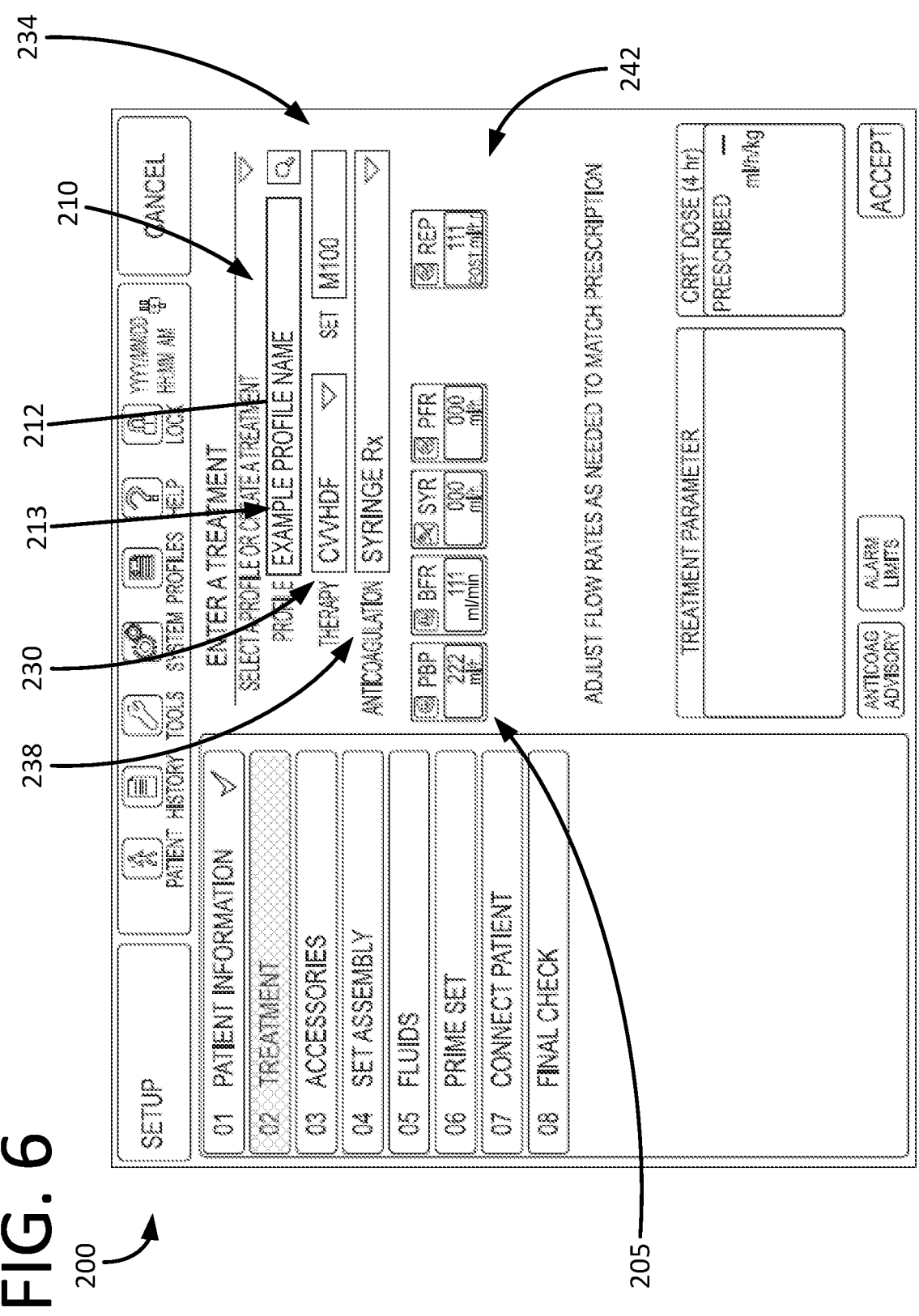

As described herein, each treatment profile may include one or more of a preset therapy type, a preset therapy set, a preset anticoagulation, and one or more preset flow rates. After a user has selected an exemplary selected profile 213, the identifier, or name, of the exemplary selected profile 213 may be displayed in the identifier area 212 of the profile identifier region 210 (as shown, "Example Profile Name" but could be another name, or identifier, such as, e.g., "Doctor-XYZ-Female-200 kgs"), a patient identifier, and the values and/or characteristics of the exemplary selected pro- file 213 may be displayed on the graphical user interface 200 as shown in FIG. 6 (such names, or identifiers, may be searchable using another field of the display).

As shown, the graphical user interface 200 may further include a therapy type region 230, therapy set region 234, an anticoagulation region 238, and a flow rate region 242. Although the profile identifier region 210, the therapy type region 230, the therapy set region 234, the anticoagulation region 238, and the flow rate region 242 are all depicted, or displayed, on the graphical user interface 200 simultane- ously or at the same time, it is to be understood that one or more of these regions may be depicted, or displayed, on the graphical user interface 200 in any combination (e.g., only one region may be displayed at a time, two or more regions may be displayed at a time, etc.). In at least one embodiment, the profile identifier region 210, the therapy type region 230, the therapy set region 234, and the anticoagulation region 238 may be displayed on the graphical user interface 200 without the flow rate region 242, and after the profile identifier region 210, the therapy type region 230, the therapy set region 234, and the anticoagulation region 238 have been selected, adjusted, etc., then the flow rate region 242 may be displayed or depicted on the graphical user interface 200 without the profile identifier region 210, the therapy type region 230, the therapy set region 234, and the anticoagulation region 238. After a profile has been selected such as the exemplary selected profile 213, the therapy type region 230 may display the preset therapy type of the exemplary selected profile 213, the therapy set region 234 may display the preset therapy set of the exemplary selected profile 213, the anticoagulation region 238 may display the preset anticoagulation of the exemplary selected profile 213, and the flow rate region 242 may display one or more preset flow rates of the exemplary selected profile 213. As shown in FIG. 6, the exemplary selected profile 213 is entitled "Example Profile Name" and includes a preset therapy type of CVVHDF (which is an acronym for Continuous Veno Venous Hemodiafiltration), a preset therapy set of M100, a preset anticoagulation type of Syringe Rx, a preset PBP (which is an acronym for pre-blood pump) flow rate of 222 milliliters per hour (mL/h), a preset BFR (which is an acronym for blood flow rate) flow rate of 111 milliliters per minute, a preset Syr (which is an acronym for syringe) flow rate of 000 mL/h, a preset PFR (which is an acronym for patient fluid removal) flow rate of 000 mL/h, and a preset Rep (which is an acronym for replacement fluid) flow (Post) rate of 111 mL/h. Although not shown, the graphical user interface 200 may further include a blood warmer target temperature region which, e.g., may also be preset by a profile.

Figure 7:
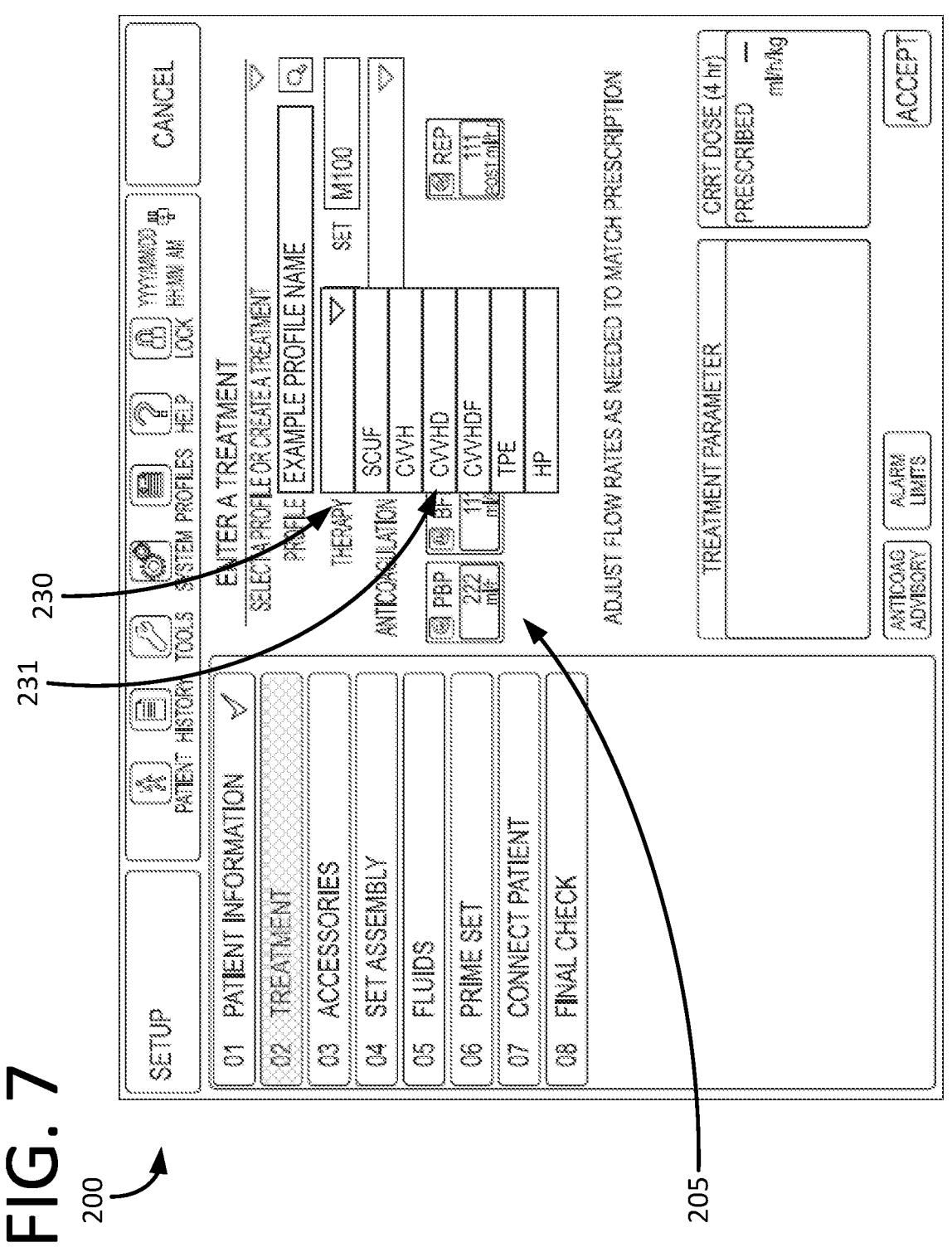

After the profile has been selected and the values and/or settings of the selected profile have been displayed in their respective regions on the graphical user interface 200, a user may modify one or more of the preset, or predefined, settings and/or values for the blood treatment defined by the selected profile 213. As shown in FIG. 7, a user may modify the therapy type by selecting the therapy type region 230, e.g., by touching the therapy type region 230 when using a touch screen. As used herein, "therapy type" may be defined as the type or kind of therapy to be performed by the extracorpo- real blood treatment system.

In this embodiment, selecting the therapy type region 230 may display a therapy list area 231 (e.g., a "pull-down" list, dialog, window, graphic element, etc.) displaying the avail- able different types of therapy. Although the disclosure herein is not limited by the therapy types described herein, the available therapy types may be slow continuous ultra- filtration (SCUF), continuous veno-venous hemofiltration, (CVVH), continuous veno-venous hemodialysis (CVVHD), continuous veno-venous hemodiafiltration (CVVHDF), therapeutic plasma exchange (TPE), HP, molecular adsor- bent recirculating system (MARS), carbon dioxide removal, etc. After the therapy list area 231 is displayed, a user may select a therapy type from the therapy list area 231, e.g., by touching a therapy type in the therapy list area 231 when using a touchscreen. After the therapy type has been selected, the therapy list area 231 may be dismissed, or disappear, and the selected therapy type may be displayed in the therapy type region 230.

Figure 8:
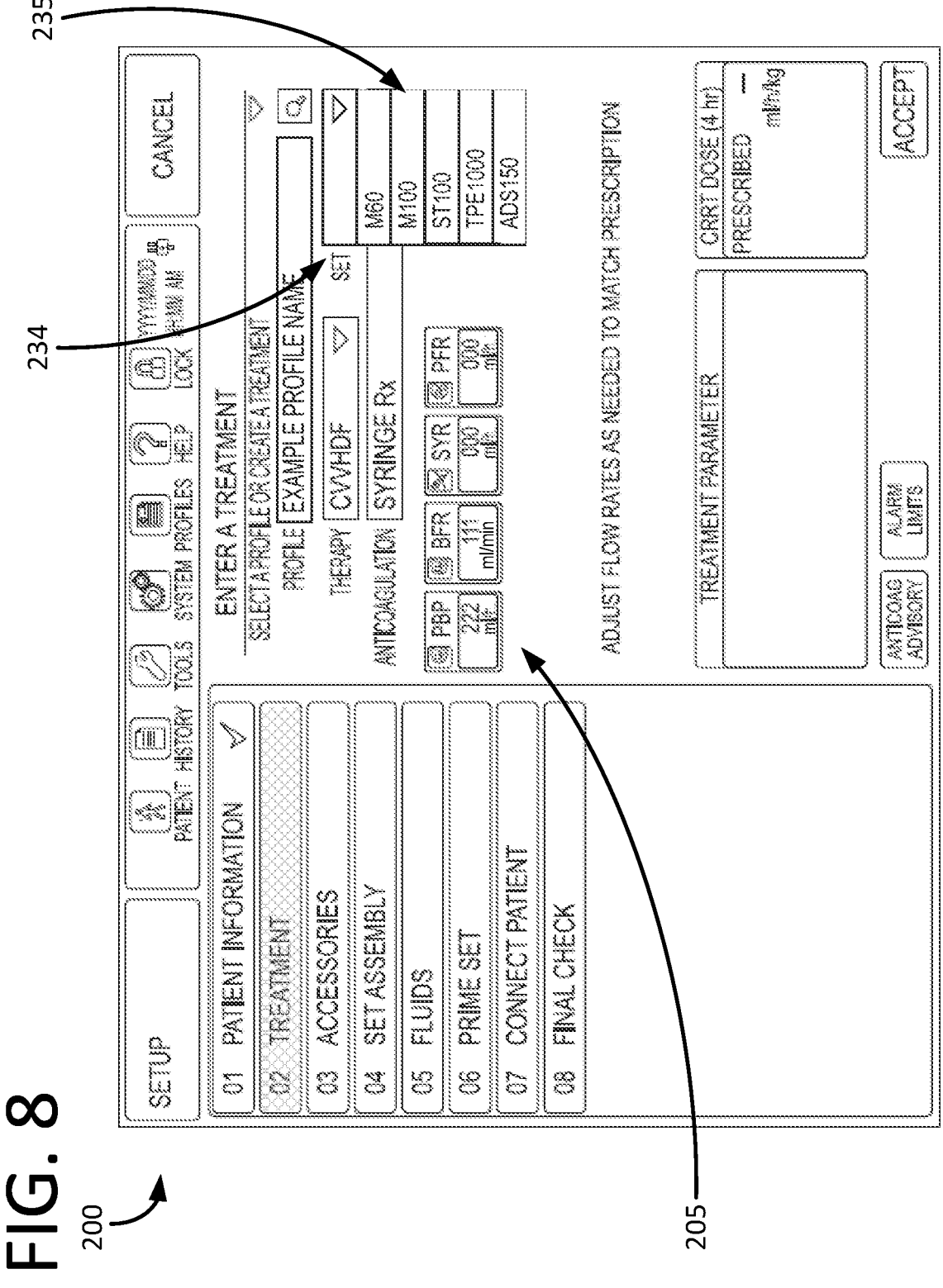

Similar to the therapy type region 230, a user may modify the therapy set by selecting the therapy set region 234, e.g., by touching the therapy set region 234 when using a touch screen, as shown in FIG. 8. In this embodiment, selecting the therapy set region 234 will display a therapy set list area 235 (e.g., a pull-down list of therapy sets) displaying the avail- able different types of therapy sets. As used herein, "therapy set" may be defined as one or more portions, or parts, of the filtration unit 120, the flow tubing lines, and the other components in the primary and secondary flow circuits 112 and 140 described herein with reference to FIGS. 2-3 (with the exception, for example, of the pumps and perhaps a few other items) that may be formed as an integral, replaceable unit (e.g., an extracorporeal blood set).

Although the disclosure herein is not limited by the therapy sets described herein, the available therapy sets may include M60, M100, ST100, TPE1000, ADS 150, M150, ST150, ST60, HF1000, HF1400, etc. After the therapy set list area 235 has been displayed, a user may select the therapy set from the therapy set list area 235, e.g., by touching a therapy set in the therapy set list area 235 when using a touchscreen. After the therapy set has been selected, the therapy set list area 235 may be dismissed, or may disappear, and the selected therapy set may be displayed in the therapy set region 234 as shown in FIG. 9.

Figure 9:
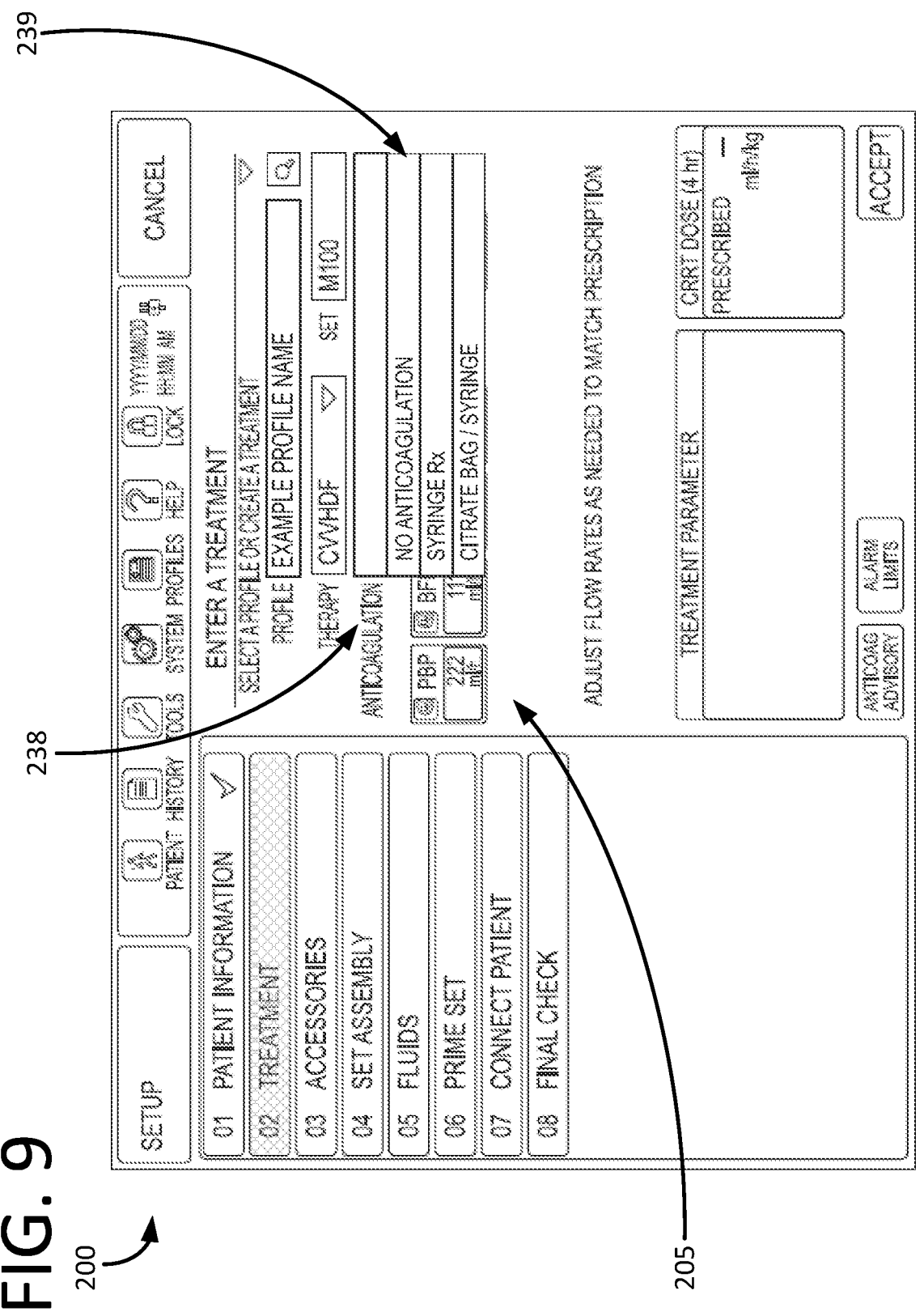

Also similar to the therapy type region 230, a user may modify the anticoagulation type by selecting the anticoagulation region 238, e.g., by touching the anticoagulation region 238 when using a touch screen, as shown in FIG. 9. As used herein, an "anticoagulation type" may be defined as the type of anticoagulation used for the treatment (e.g., such as the type of anticoagulation, whether citrate is to be used, whether calcium is to be infused, whether heparin is to be used, whether low molecular weight heparin is to be used, whether prostacyclin is to be used, etc.). In this embodiment, selecting the anticoagulation region 238 may display an anticoagulation list area 239 (e.g., a pull-down list, etc.) displaying the available different types of anticoagulation. Although the disclosure herein is not limited by the types of anticoagulation described herein, the available types of anticoagulation as shown in FIG. 9 may be No Anticoagulation, Syringe Rx, Citrate Bag/CA Syringe, etc. After the list of available types of anticoagulation have been displayed, a user may select an anticoagulation type from the anticoagulation list area 239, e.g., by touching the anticoagulation type in the anticoagulation list area 239 when using a touchscreen. After the anticoagulation type has been selected, the anticoagulation list area 239 may be dismissed, or may disappear, and the selected anticoagulation type may be displayed in the anticoagulation region 238 as shown in FIG. 10.

Figure 10:
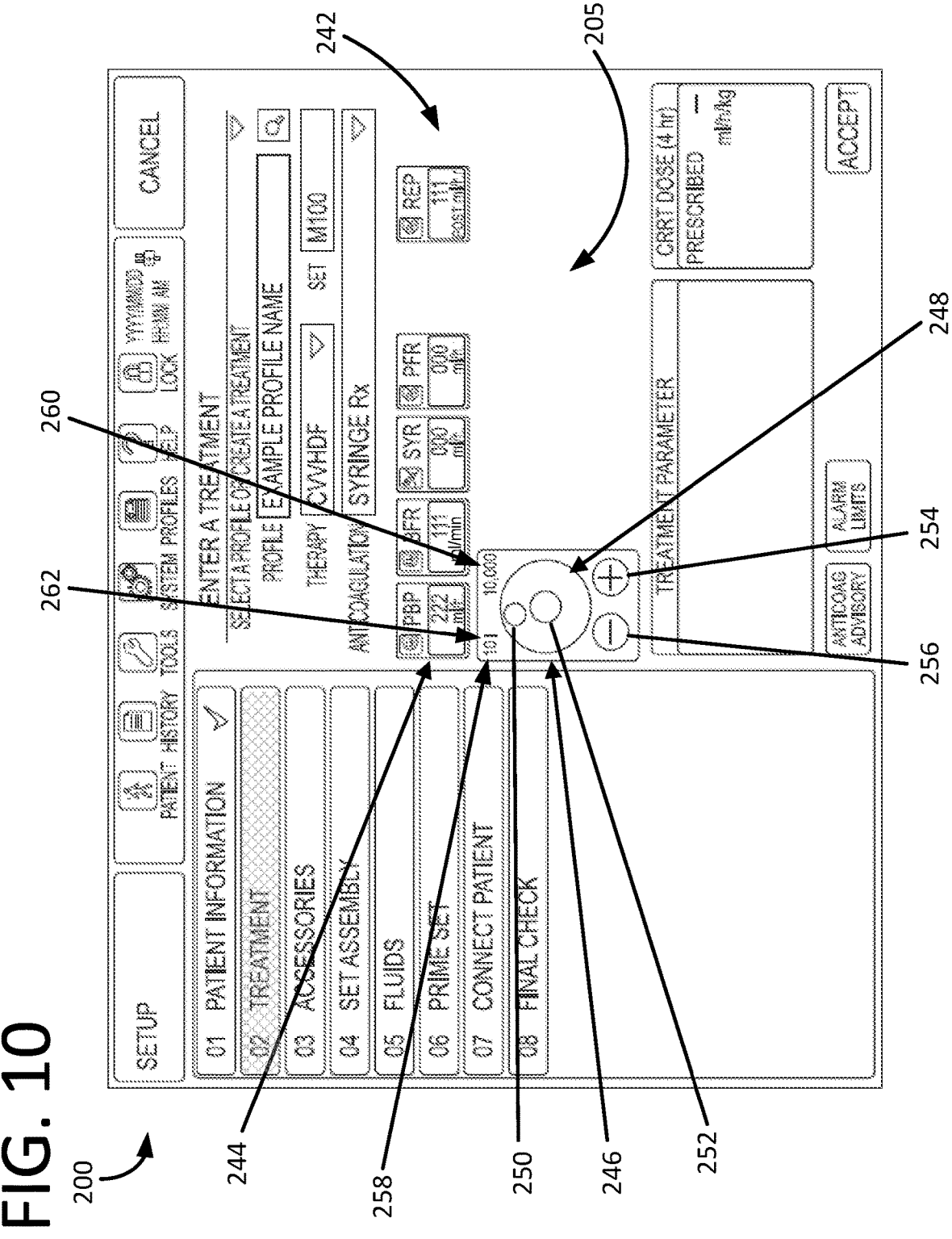

Further, one or more preset, or predefined, flow rates of a selected profile may be adjusted or modified as shown in FIG. 10. Such one or more flow rates may correspond to the selected profile and the presets or settings of the selected profile such as therapy type, therapy set, and anticoagulation type. Although an exemplary system and method may include flow rates for a plurality of different solutions, each profile may only include flow rates for a selected set of solutions, and thus, only the flow rates for a selected set of solutions may be displayed for a selected profile. In other words, some solutions may be only depicted if a particular therapy type, therapy set, and/or anticoagulation type are selected. For example, in at least one embodiment, some solutions may only be selected or adjusted if citrate anticoagulation is being used.

A user may adjust a specific flow rate by selecting a flow rate display area for the desired specific flow rate displayed in the flow rate region 242 (e.g., by touching the specific flow rate area in the flow rate region 242). As shown in FIG. 10, PBP has been selected by selecting (e.g., touching) the PBP flow rate display area 244, and in response to the selection, a flow rate adjustment area 246 may be displayed proximate the PBP flow rate display area 244. Although the flow rate adjustment area 246 is displayed below the PBP flow rate display area 244, it is to be understood that the flow rate adjustment area 246 may be located anywhere on the graphical user interface 200 (e.g., as a pop-up dialog, a pop-over area or window, etc.).

A user may use the flow rate adjustment area 246 to adjust, or modify, the flow rate of the selected item. In this embodiment, the flow rate adjustment area 246 may include a rotary portion 248 that may be used to adjust the flow rate. For example, a user may select an outer smaller circle 250 of the rotary portion 248 and drag, or move, the outer smaller circle 250 around a central, inner circle 252 of the rotary portion 248 similar to a crank or a dial. Moving the outer smaller circle 250 clockwise around the central inner circle 252 may increase the flow rate while moving the outer smaller circle 250 counterclockwise around the central inner circle 252 may decrease the flow rate.

As the PBP flow rate is adjusted, the PBP flow rate displayed in the PBP flow rate display area 244 may be updated to reflect the adjusted value (e.g., the PBP flow rate displayed in the PBP flow rate display area 244 may change while a user is adjusting the PBP flow rate using the flow rate adjustment area 246). Further, while a flow rate is being modified, the previous flow rate (e.g., the flow rate prior to any modification or adjustment) may also be indicated on the graphical user interface 200. For example, the previous flow rate may be indicated in smaller text next to the flow rate displayed in the flow rate display area such as the PBP flow rate display area 244.

Additionally, the flow rate adjustment area 246 may include a plus button 254 and a minus button 256 that may be selected by a user to increment and decrement, respectively, the flow rate. Further, a range of available flow rates may be indicated by a lower range number 258 (10 mL/h as shown) located in the upper left of the flow rate adjustment area 246 and an upper range number 260 (10,000 mL/h as shown) located in the upper left of the flow rate adjustment area 246. Further, the current flow rate (e.g., the flow rate being adjusted) may be indicated within the range by line 262 located (proportionally located based on the selected flow rate) between the upper and lower range numbers 258, 260.

Figure 11:
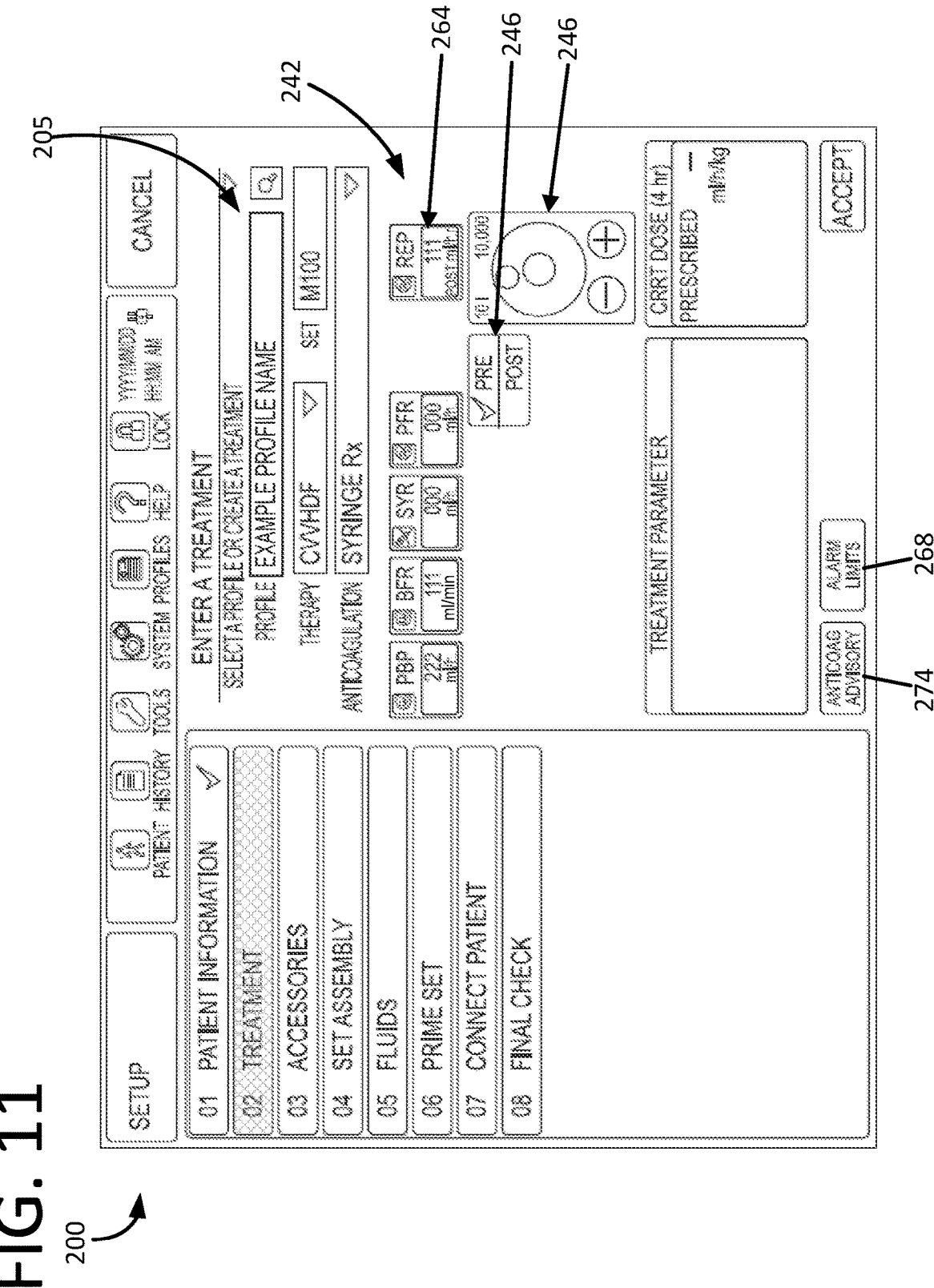

After a specific flow rate has been adjusted or modified, a user may proceed to modifying or adjusting another flow rate in a similar manner or any other displayed setting or parameter. As shown in FIG. 11, a user has selected the Rep flow rate by selecting the Rep flow rate display area 264 in the flow rate region 242, and consequently, a flow rate adjustment area 246 has been displayed on the graphical user interface 200 proximate (e.g., below) the Rep flow rate display area 264.

Additionally, the selection of a specific flow rate in the flow rate region 242 may further display additional graphical areas that may be used to adjust, or modify, one or more parameters related to the selected specific flow rate. For example, as shown in FIG. 11, a Pre/Post selection area 266 has been displayed upon selection of the Rep flow rate. The Pre/Post selection area 266 may be used to set flow rates for different periods of the blood treatment time period.

Figure 12:
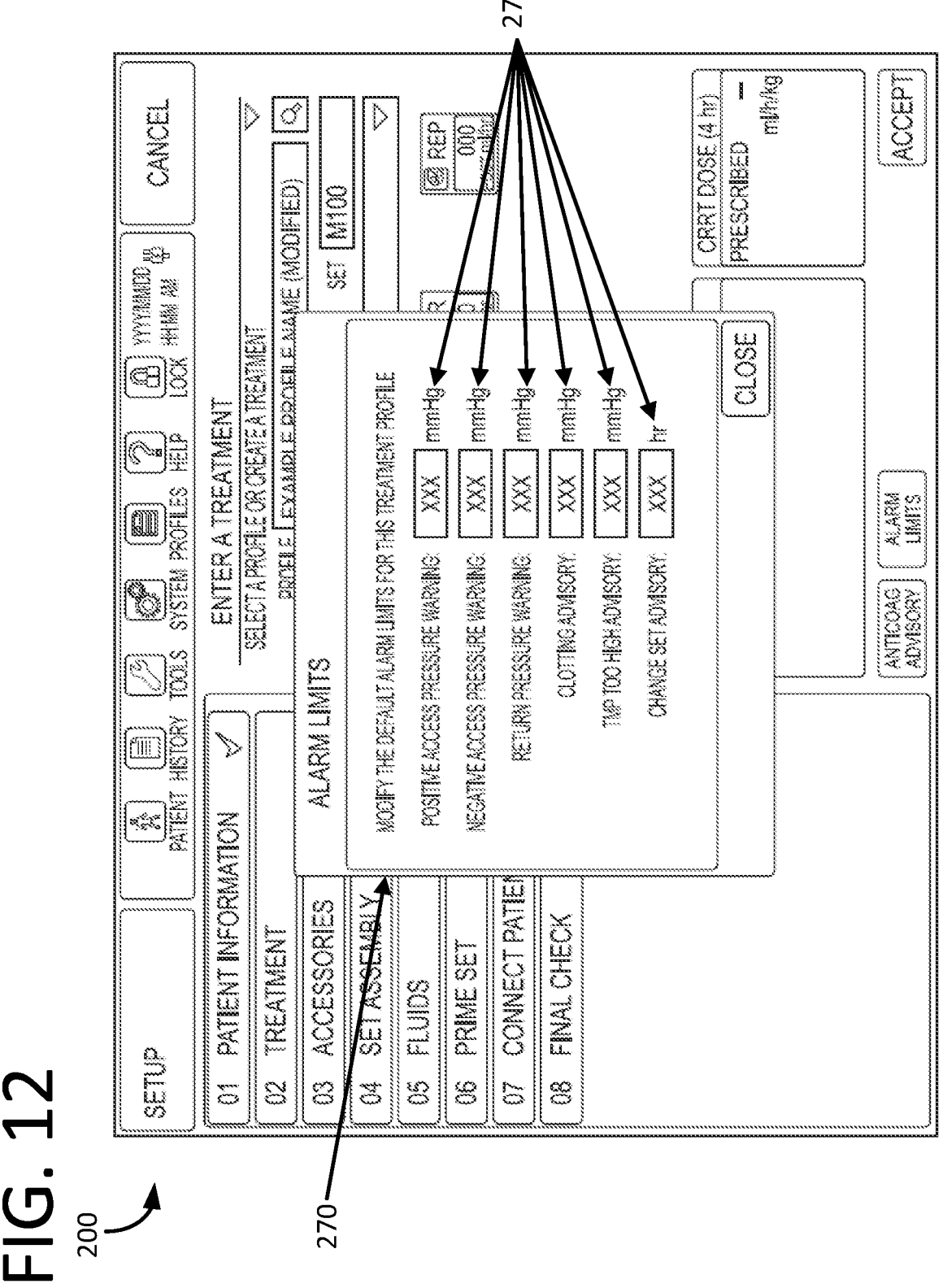

A user may also adjust one or more preset alarm limits and/or one or more preset anticoagulation advisory values for a selected profile. For example, a user may select (e.g., touch, click, etc.) an "Alarm Limits" area, or button, 268 as shown in FIG. 11 to display an alarm region 270 as shown in FIG. 12. The alarm region 270 may display one or more (e.g., a plurality) of preset alarm limits 272. As used herein, "alarm limits" may be defined as values of certain monitored parameters that may be used to initiate, or trigger, one or more alarms. When a monitored parameter exceeds, or crosses, an alarm limit, an alarm may be triggered to alert an operator or clinician. As shown, the one or more preset alarm limits 272 may include "Positive Access Pressure Warning," "Negative Access Pressure Warning," "Return Pressure Warning," "Clotting Advisory," TMP Too High Advisory," and "Change Set Advisory." Each of the alarm limits 272 may be adjusted by selecting a specific alarm limit which may display an alarm limit adjustment area (e.g., window, dialog, etc.) that may, e.g., be similar to the flow rate adjustment area 246.

Further, for example, a user may select (e.g., touch, click, etc.) an "Anticoag Advisory" area, or button, 274 as shown in FIG. 11 to display an anticoagulation advisory region that may include one or more preset anticoagulation advisories such as, e.g., time to empty, etc. As used herein, an "anticoagulation advisory" may be defined as a setting, or threshold, to trigger, or initiate an advisory with respect to anticoagulation used in an extracorporeal blood treatment. The anticoagulation advisory adjustment region may appear similar to the alarm region 270 but include anticoagulation advisories as opposed to alarm limits.

One or more settings or presets of a treatment profile that are added or adjusted may conflict with the system being used, the inventory of the clinic, etc. For example, the system being used may not be able to support each of the settings or presets of the treatment profile. Further, for example, the clinic within which the system is used may not include the inventory to support each of the settings or presets of the treatment profile. If the treatment profile is in conflict, the graphical user interface 200 may block a user from proceed, e.g., by graying out the "Accept" area located in the lower right of the graphical user interface 200. Additionally, if the treatment profile is in conflict, the graphical user interface 200 may display a rationale (e.g., reason or explanation of why the treatment profile is in conflict) to the user in a treatment parameter area or box, e.g., as shown in the bottom of the profile region 205 in FIG. 9. In other words, if a conflict exists between one or more solutions in the profile and the solutions of the extracorporeal blood treatment system, then the profile may not be allowed.

The computing apparatus 12 of the exemplary extracorporeal blood treatment system 10 may be further configured to allow a user to create and/or modify one or more profiles for use in performing extracorporeal blood treatment, as opposed to selected a treatment profile already created and stored in the system described herein with respect to FIGS. 4-12. Screenshots depicting exemplary graphical user interfaces for use in creating and/or modifying one or more treatment profiles (e.g., to be stored in the system) are depicted in FIGS. 13-17. Such exemplary graphical user interfaces may be depicted by the display apparatus 22 of the system 10 described herein with reference to FIG. 1 and/or the display screen 161 of FIGS. 2-3.

Figure 13:
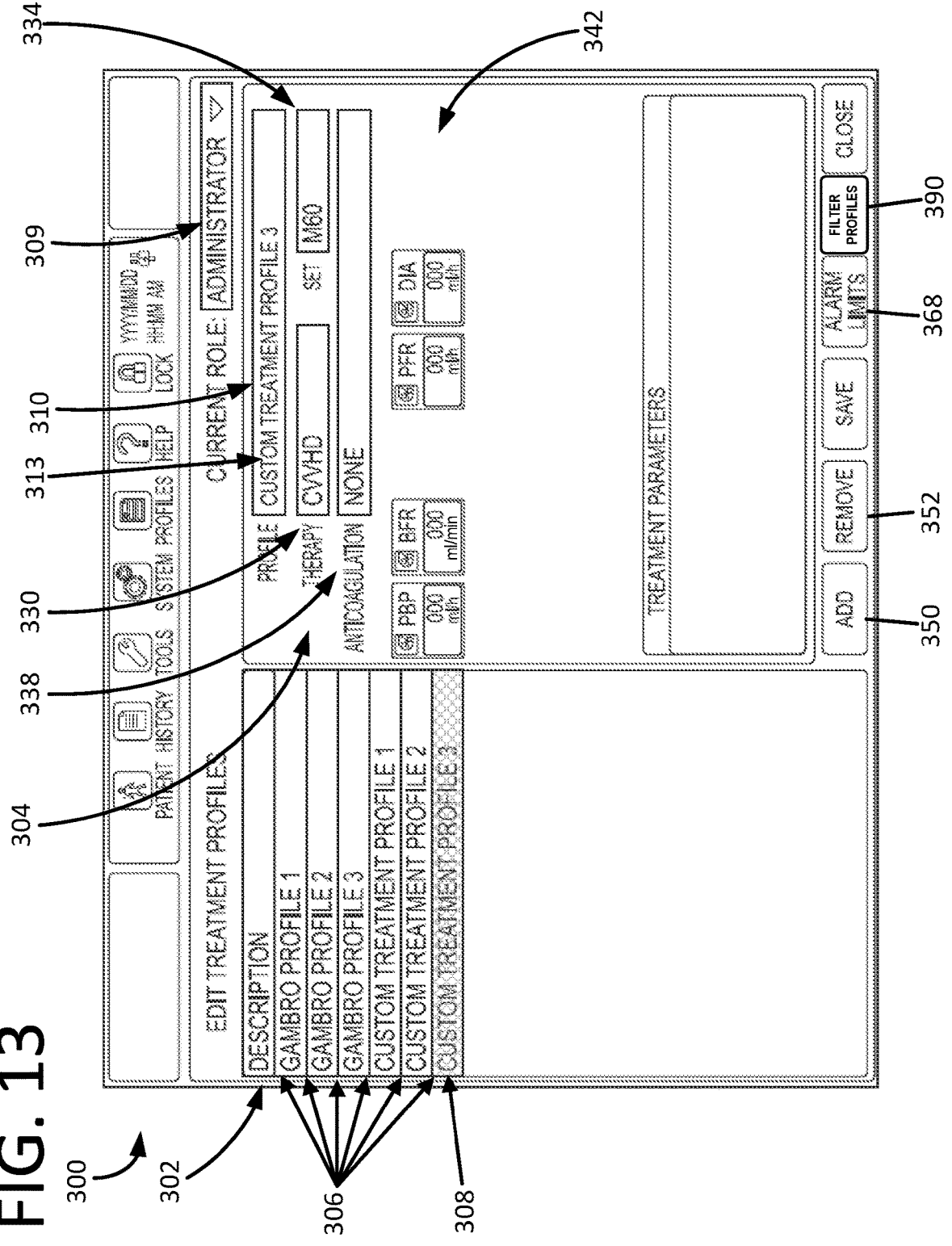
FIGS. 13-17 are screenshots of graphical user interfaces for use in creating and/or modifying treatment profiles in extracorporeal blood treatment systems, for example, such as shown generally in FIGS. 1-3.

An exemplary profile creation/modification graphical user interface 300 that may be used in the creation and/or modification of one or more profiles is depicted in FIG. 13. To display or access the profile creation/modification graphical user interface 300, a user may need elevated privileges (e.g., access privileges for security). For example, a user may need to be "logged on" as a more privileged user, or power user, such that the profile creation/modification graphical user interface 300 is available. Such privileged access to the profile creation/modification graphical user interface 300 may be designed to stop less privileged clinicians (e.g., nurses) from being able to create and/or modify the one or more profiles and to allow only more privileged clinicians (e.g., doctors) to create and/or modify the one or more profiles. For example, as shown in FIG. 13, a user may change their privilege by selecting a privilege region 309. As shown, the privilege region 309 displays "Administrator," which indicates that an administrator user (e.g., a user that has elevated privileges to create and/or modify treatment profiles) is logged in.

To navigate to the profile creation/modification graphical user interface 300, a user may select a "Profiles" area, or button, 290 located within a toolbar region 292 of the exemplary graphical user interface 200 as shown in FIG. 4, which may prompt the display of the profile creation/modification graphical user interface 300. However, any navigational region, or portion, may be used to display the graphical user interface 300 with the graphical user interface 200 (e.g., on the same screen at the same time) or separately from the graphical user interface 200. The profile creation/modification graphical user interface 300 may include a profile selection region 302 located on the left side of the graphical user interface 300 and a profile region 304 located on the right side of the graphical user interface 300.

The profile region 304 of the graphical user interface 300 may be similar to the profile region 205 of the graphical user interface 200. For example, the profile region 304 may include a profile identifier region 310, a therapy type region 330, a therapy set region 334, an anticoagulation region 338, a fluid rate region 342, and an "Alarm Limits" area, or button, 368 that may be similar to the profile identifier region 210, the therapy type region 230, the therapy set region 234, the anticoagulation region 238, the fluid rate region 342, and the "Alarm Limits" area, or button, 268, respectively, of the graphical user interface 200 described herein with reference to FIGS. 4-12. Although the profile identifier region 310, the therapy type region 330, the therapy set region 334, the anticoagulation region 338, and the flow rate region 342 are all depicted, or displayed, on the graphical user interface 300 simultaneously or at the same time, it is to be understood that one or more of these regions may be depicted, or displayed, on the graphical user interface 300 in any combination (e.g., only one region may be displayed at a time, two or more regions may be displayed at a time, etc.). In at least one embodiment, the profile identifier region 310, the therapy type region 330, the therapy set region 334, and the anticoagulation region 338 may be displayed on the graphical user interface 300 without the flow rate region 342, and after the profile identifier region 310, the therapy type region 330, the therapy set region 334, and the anticoagulation region 338 have been selected, adjusted, etc., then the flow rate region 342 may be displayed or depicted on the graphical user interface 300 without the profile identifier region 310, the therapy type region 330, the therapy set region 334, and the anticoagulation region 338.

The graphical user interface 300, however, is configured to allow a user to create one or more treatment profiles and save such one or more profiles into the system for later use during preparation of the system for an extracorporeal blood treatment. Further, the graphical user interface 300 may also be configured to allow a user to modify one or more already saved profiles and save the profiles as modified (e.g., with the changes, or modifications, made to the profile using the graphical user interface 300 and provided with a different name or identifier).

To modify an existing profile, a user may select an existing profile using the profile selection region 302. The profile selection region 302 may include a list of profiles 306 (e.g., listed by name, therapy type, therapy set, disease type, etc.). When a user selects a profile, the profile may be indicated as being selected in the graphical user interface and the preset, or predefined, values for the selected profile may be displayed in the profile region 304. For example, when the exemplary selected profile 308 entitled "Custom Treatment Profile 3" has been selected, it may be highlighted as shown in FIG. 13, and the preset, or predefined, values for the selected profile 308 may be displayed in the profile region 304. The selected profile 308 may then be modified. More specifically, one or more preset values and/or settings of the selected profile 308 may be changed.

Further, at least one of the profiles stored on the system and listed in the profile selection region 302 may be protected from deletion or modification of one or more settings. In other words, such protected profiles may not be deleted by a user or one or more settings may not be modified by a user. For example, at least one of an identifier, preset therapy type, and preset therapy set of a protected profile may not be modifiable by a user.

Figure 14:
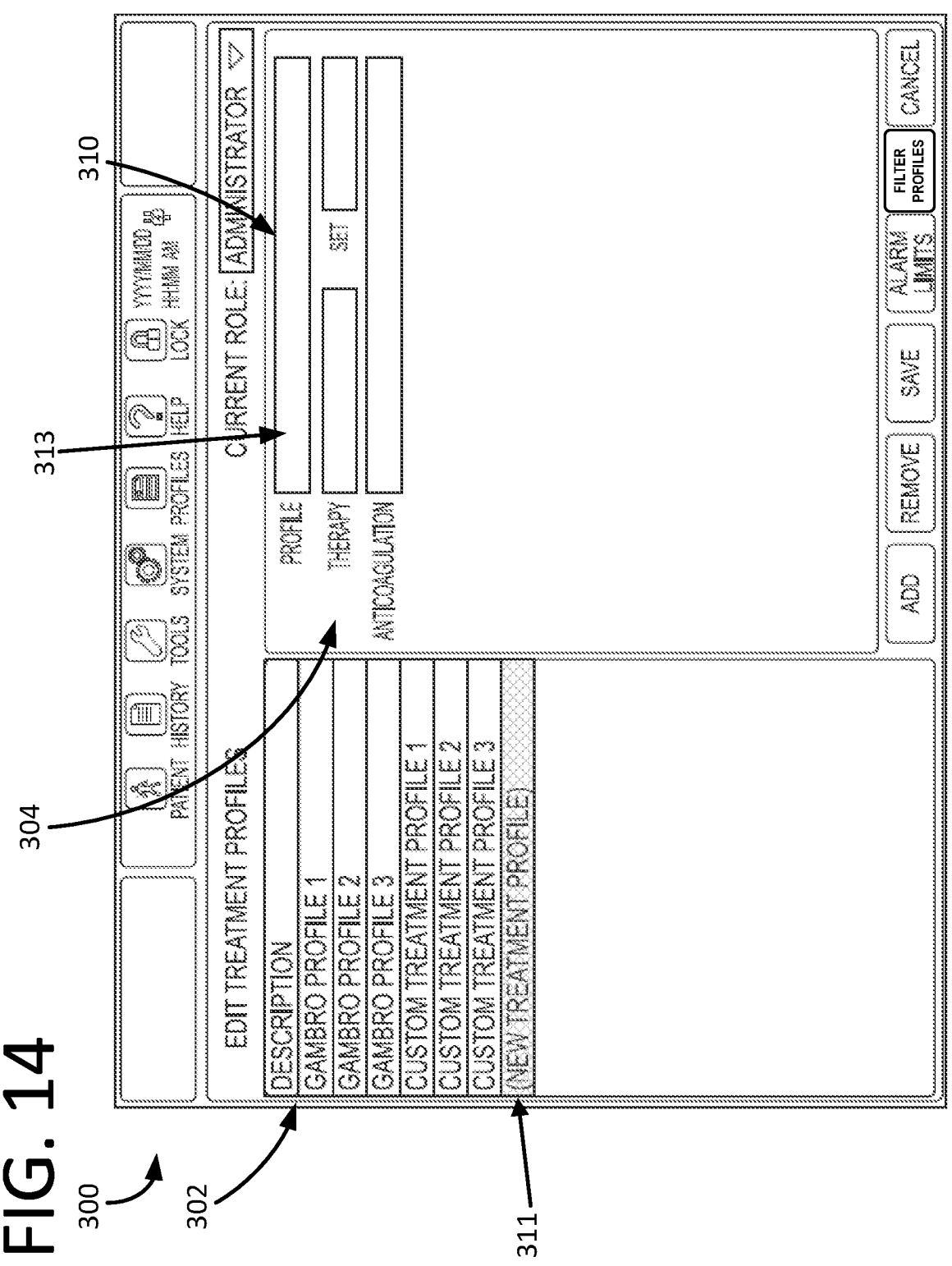

To create a new profile, a user may select the "Add" area, or button, 350 located near the bottom of the graphical user interface 300. As shown in FIG. 14, selection of the "Add" area, or button, 350 may display a new profile 311, i.e., "(New Treatment Profile)," in the profile selection region 302 and blank, or neutral, settings and/or values for the new profile in the profile region 304. The new profile may then be created. More specifically, one or more values and/or settings of the new profile may be selected or set (e.g., filled in, selected from pull-down menus, etc.).

To remove a profile, a user may select a profile in the profile selection region 302 and may select the "Remove" area, or button, 352 located near the bottom of the graphical user interface 300. In one or more embodiments, the graphical user interface 300 may display a confirmation region such that the user may confirm that they would like to remove the highlighted profile. The confirmation region may be, e.g., a pop-up window or dialog.

The modification of an existing profile and the creation of a new profile using the graphical user interface 300 may be similar in that each setting or value for the existing profile and the new profile may be changed. FIGS. 14-18 depict the creation of a new profile using the graphical user interface 300. It is to be understood that a profile may be modified using the same or similar processes and/or interfaces as shown in FIGS. 14-17 except that instead of displaying void, or blank, values or settings of the new profile, the graphical user interface 300 may display the preset, or predefined, settings of the selected profile to be modified (e.g., to create a new profile).

The identifier of the new profile 311 may be modified by selecting the profile identifier region 310 of the profile region 304. Upon selection of the profile identifier region 310, the graphical user interface may provide a graphic region or area to input a new identifier for the new profile 311.

Figure 15:
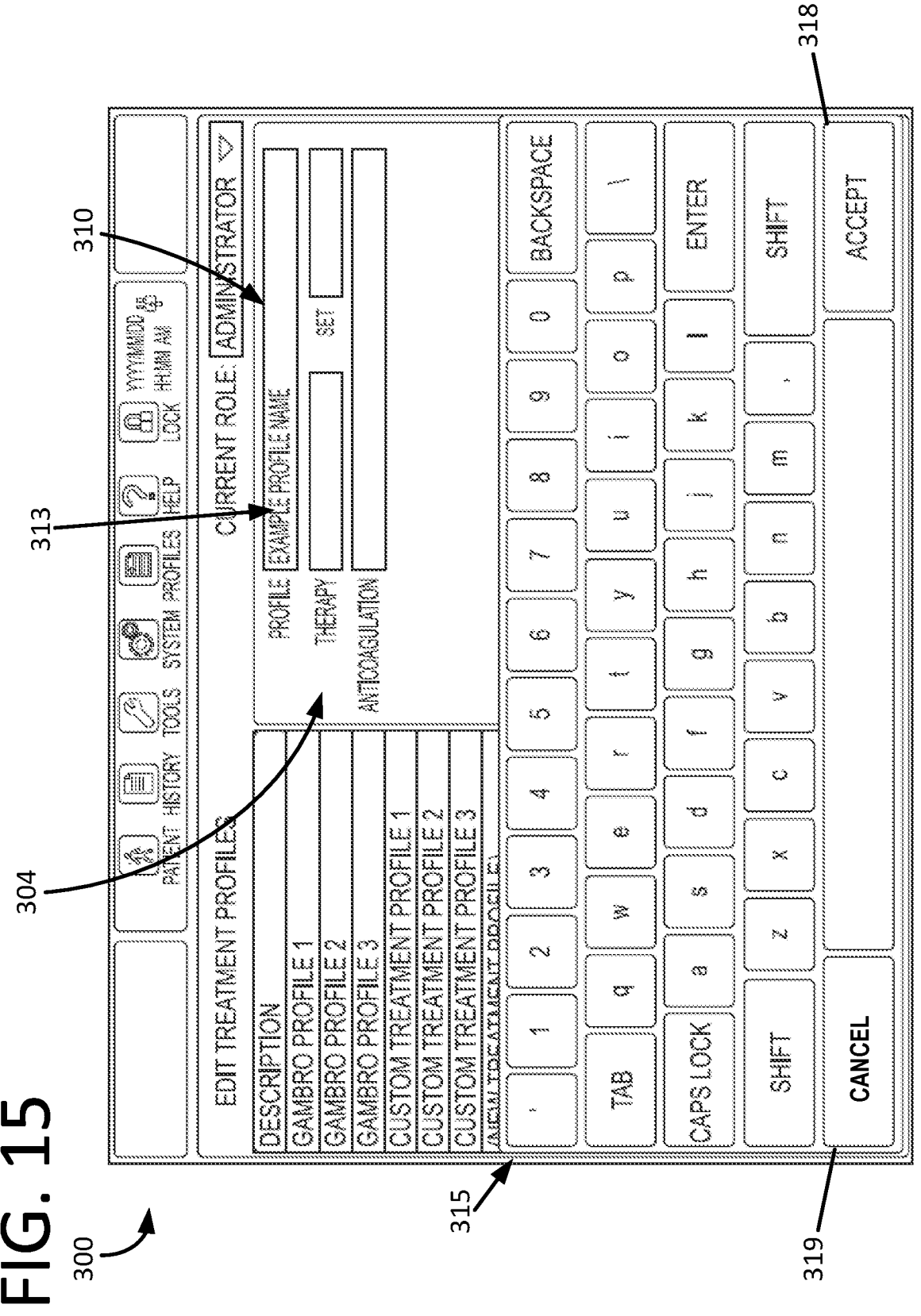

An exemplary profile identifier modification region 315 is depicted in FIG. 15. The modification region 315 includes a touchscreen keyboard configured such that a user may select one or more letters of the keyboard to input a new identifier in the profile identifier region 310. As shown, the identifier of the new profile 311 has been modified to be "Example Profile Name." After a user has finished modifying the identifier 313 of the new profile 311, the user may select the "Accept" area, or button, 318 located on the keyboard of the modification region 315, which may dismiss the modification region 315 from the graphical user interface 300. Additionally, if a user decides to cancel, or stop, modifying the identifier, the user may select the "Cancel" area, or button, 319 located on the keyboard of the modification region 315, which may also dismiss the modification region 315 from the graphical user interface 300 but without accepting any changes to the profile identifier 313.

The therapy type, therapy set, anticoagulation type, and one or more flow rates of the new profile 311 may be modified (e.g., modified from a blank, or null, value or setting) similar to how the therapy type, therapy set, anticoagulation type, and one or more flow rates of the selected profile 213 is modified as described herein with reference to FIGS. 4-12, and as such, the modification processes and functionality as well as the graphic regions/areas will not be described further herein in detail. In other words, the profile region 304 of the graphical user interface 300 may include similar profile modification processes and functions as well as graphic regions/areas as the graphical user interface 200 as described herein with reference in FIGS. 4-12.

Figure 16:
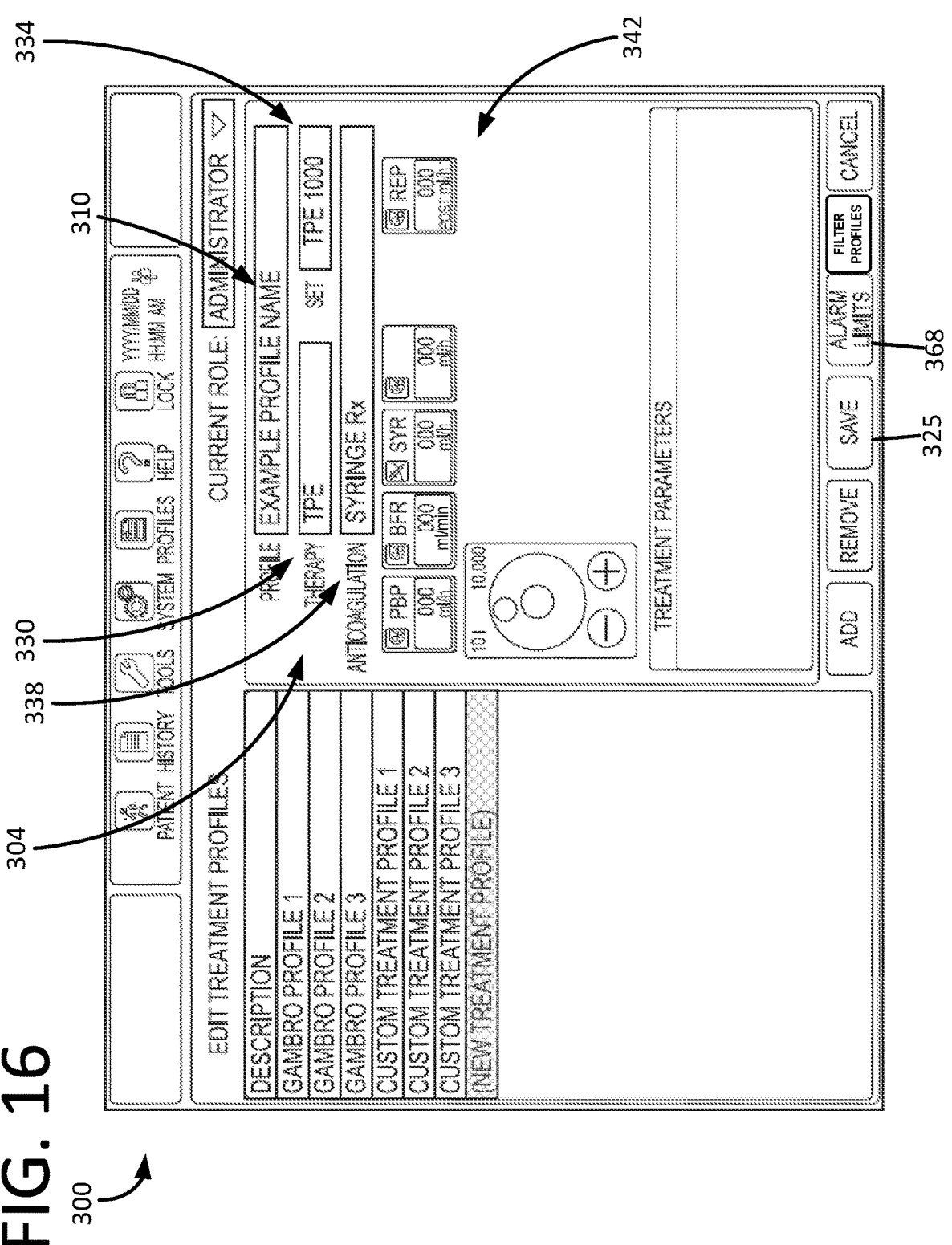

As shown in FIG. 16, a user has created a new profile 311 entitled "Example Profile Name" as shown in the profile identifier region 310. The new profile 311 includes a therapy type of TPE as shown in the therapy type region 330, a therapy set of TPE1000 as shown in the therapy set region 334, an anticoagulation type of Syringe Rx as shown in the anticoagulation region 338, and a PBP flow rate of 222 ml/h as shown in the flow rate region 342.

After a new profile has been created or a profile has been modified, a user may select a "Save" area, or button, 325 of the graphical user interface 300. In one or more embodiments, to save a newly-created profile or a modified profile, one or more settings or values of newly-created or modified profile may need to be set. For example, each profile may be required to include at least a therapy type and a therapy set to be saved, and if a newly-created profile or a presently-modified profile does not include one of a therapy type and a therapy set, the graphical user interface 300 may not allow a user to save the profile as created or modified. In at least one embodiment, the graphical user interface may provide this functionality by not making the "Save" button available to the user (e.g., by providing no interaction when selected, "greying-out" the button, etc.) when one of a therapy type and a therapy set is not preset.

Figure 17:
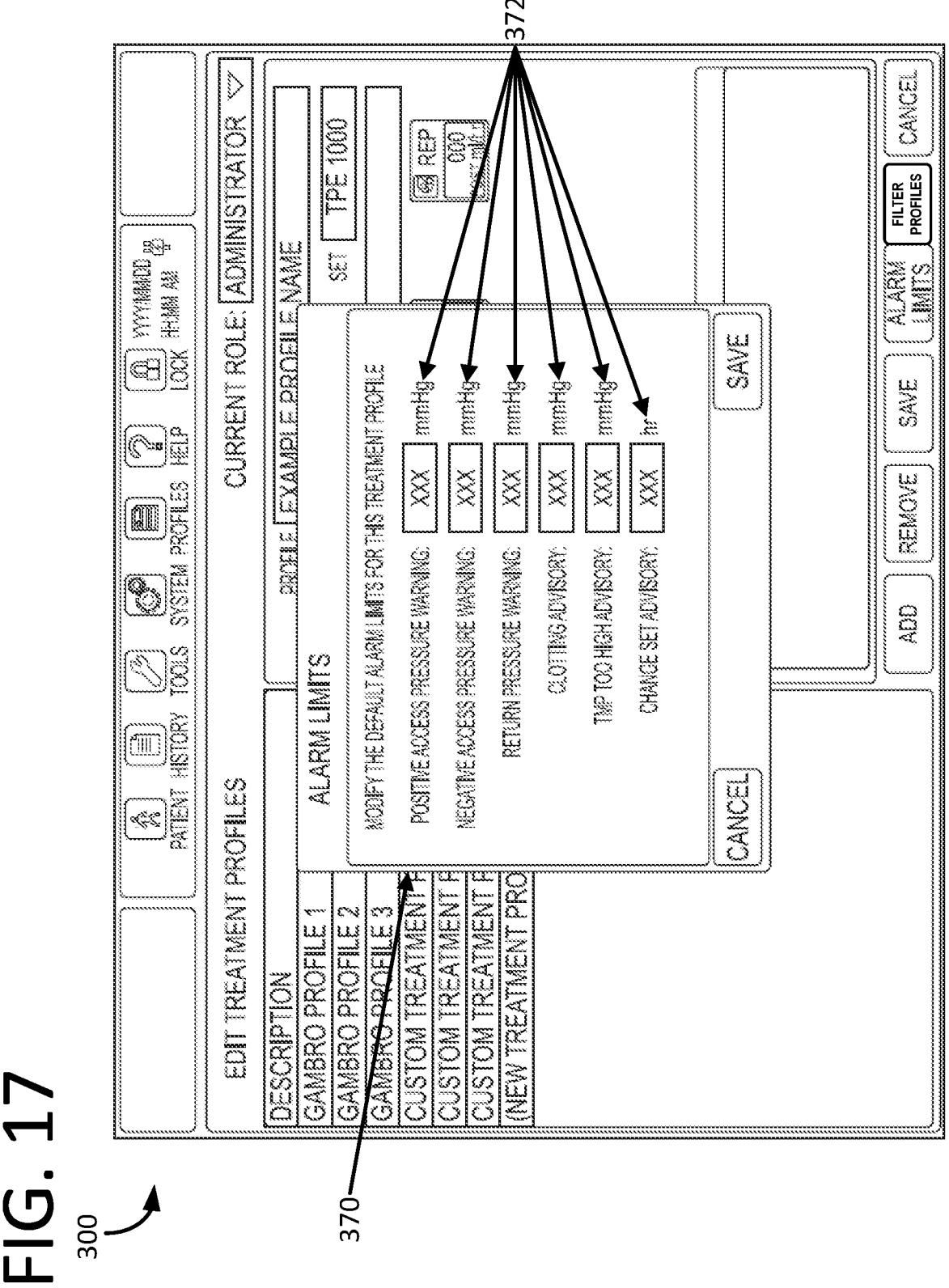

Additionally, a user may also adjust one or more alarm limits for the new selected profile 311. For example, a user may select (e.g., touch, click, etc.) an "Alarm Limits" area, or button, 368 as shown in FIG. 16 to display an alarm region 370 as shown in FIG. 17. The alarm region 370 may display one or more (e.g., a plurality) of alarm limits 372. As shown, the one or more alarm limits 372 may include "Positive Access Pressure Warning," "Negative Access Pressure Warning," "Return Pressure Warning," "Clotting Advisory," TMP Too High Advisory," and "Change Set Advisory." Each of the alarm limits 372 may be adjusted by selecting a specific alarm limit which may display an alarm limit adjustment area (e.g., window, dialog, etc.) that may, e.g., be similar to the flow rate adjustment area 246.

Filter profile information for use with the profile filter region described herein with reference to the profile selection region 216 may be modified or added to a treatment profile using the graphical user interface 300. For example, a user may select a treatment profile 306 using the treatment profile selection region 302 and select a filter properties area, or button, 390 as shown in FIG. 13. Selecting the filter properties area 390 may present a filter properties input region configured to allow a user to input identification data for the selected profile such as, e.g., prescribing doctor, weight, age, gender, disease state, location, intracellular volume, etc. Such identification data may then be used to sort, or filter, the stored profiles when using the profile selection 216 described herein within reference to FIG. 5.

Figure 18:
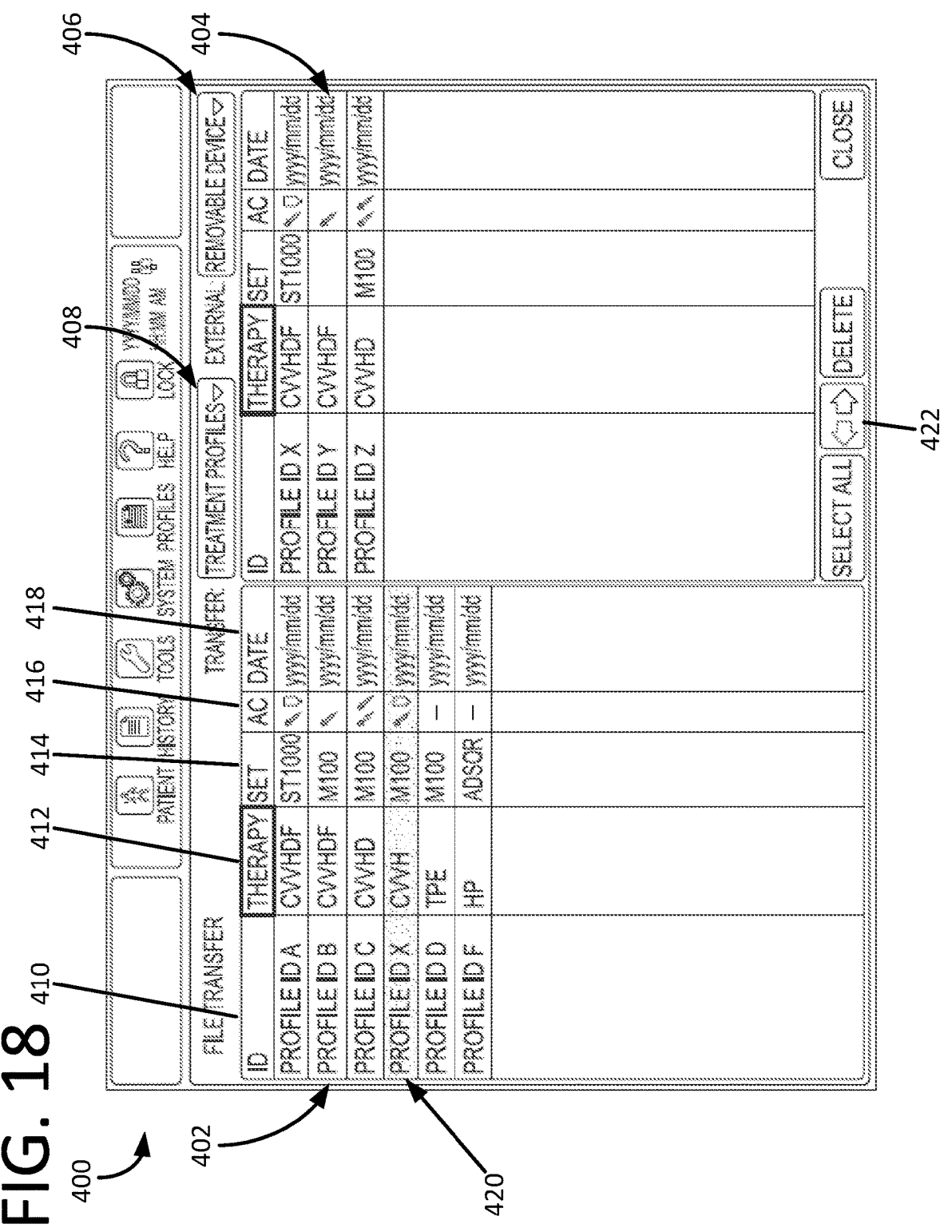
FIG. 18 is a screenshot of a graphical user interface for use in transferring treatment protocols to and from extracorporeal blood treatment systems, for example, such as shown generally in FIGS. 1-3.

Treatment profiles may be transferred to and from exemplary extracorporeal blood treatment systems, e.g., for storage or record-keeping purposes, for transfer to another machine, etc. An exemplary graphical user interface 400 for use in transferring treatment protocols to and from exemplary extracorporeal blood treatment systems is depicted in FIG. 18. The graphical user interface 400 includes a local profile list region 402 and an external profile list region 404. The local profile list region 402 may be configured to list the plurality of treatment profiles stored on the extracorporeal blood treatment system. In other words, the local profile list region 402 shows the treatment profiles stored locally, or on the system that is displaying the graphical user interface 400.

Various information for each displayed, stored profile may be further shown, or displayed, in the profile list region. As shown, the identifier of each profile is located in an "ID" column 410, the therapy type of each profile is located in a "Therapy" column 412, the therapy set of each profile is located in a "Set" column 414, the anticoagulation type of each profile is located in a "AC" column 416, and the date that each profile was lasted used is located in "Date" column 418. Additionally, although the date of creation for each profile may not be displayed as shown, each profile may further include its date of creation, and may be depicted in one or more profile list regions.

Likewise, the external profile list region 404 may be configured to list the plurality of treatment profiles stored on an external device (e.g., external, or separate from, the extracorporeal blood treatment system) such as, e.g., a memory card, a Universal Serial Bus memory stick, another extracorporeal blood treatment system, a computer, etc. that is operatively connected (e.g., via a network, internet, cloud, servers, etc.) to the extracorporeal blood treatment system. In other words, the external profile list region 404 shows the treatment profiles not stored locally, or on the system that is displaying the graphical user interface 400, but that are located, for example, on a device or apparatus that is operatively coupled to the extracorporeal blood treatment system.

In at least one embodiment, the extracorporeal blood treatment system may include a data port such as Universal Serial Bus (USB) port and a USB memory stick may be coupled to such USB port for transfer of treatment profiles.

To transfer one or more profiles from the extracorporeal blood treatment system to the external device, or vice versa, a user may select the profiles that they would like to transfer (e.g., by touching the profiles, by clicking the profiles, etc.) and then selecting the transfer area, or button, 422 located near the bottom of the graphical user interface 400. As shown, an arrow pointing leftward is highlighted within the transfer button 422 indicating the direction of the transfer, e.g., from the extracorporeal blood treatment system to the external device, from the external device to the extracorporeal blood treatment system, etc.

Additionally, the graphical user interface 400 may further include an external device selection region 406 configured to allow a user to select which external device's (e.g., of the external devices coupled to the system) contents should be displayed in the external profile list region 404. As shown, the external device is a "Removable Device" such as a USB memory stick. After the external device selection region 406 has been selected, another region such as a window or dialog may appear on the graphical user interface 400 by which a user may select what external device's contents should be displayed in the external profile list region 404.

Further, the graphical user interface 400 may also be configured to transfer other data such as, e.g., historical data, performance data, settings, processes, etc. to and from the extracorporeal blood treatment system to an external device. As shown, a user may select a transfer type region 408 to display another region such as a window or dialog on the graphical user interface 400 configured to allow a user to select what type of data should be shown in the list regions 402, 404. In other words, the transfer type region 408 may provide a filtering function configured to only show the selected type of data on the extracorporeal blood treatment system and the external device while filtering out the unselected type of data (e.g., filter by physician). As shown in FIG. 18, the "Treatment Profiles" transfer type has been selected, and as such, only treatment profiles have been displayed in each list region 402, 404.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A method for an extracorporeal blood treatment system comprising:

providing an extracorporeal blood control apparatus to perform an extracorporeal blood treatment, the extracorporeal blood control apparatus comprising one or more pumps;

storing a plurality of profiles including preset settings for an extracorporeal blood treatment, wherein each profile of the plurality of profiles comprises an identifier, at least a preset therapy type of a plurality of different therapy types, and a preset therapy set of a plurality of different therapy sets, each therapy set being a replacement unit for use in performing a different therapy;

providing a graphical user interface comprising a profile identifier region, a therapy type region, therapy set region, an accept area, and a save area;

providing an input apparatus configured to allow a user to select a profile of the plurality of profiles using the profile identifier region of the graphical user interface;

allowing a user to use the input apparatus to select a profile of the plurality of profiles using the profile identifier region of the graphical user interface;

displaying on the graphical user interface the preset therapy type of the selected profile in the therapy type region and the preset therapy set of the selected profile in the therapy set region in response to selection of the selected profile of the plurality of profiles;

allowing a user to use the input apparatus to modify one or more of:

the preset therapy type of the selected profile to a different therapy type of the plurality of different therapy types using the therapy type region of the graphical user interface, and the preset therapy set of the selected profile to a different therapy set of the plurality of different therapy sets using the therapy set region of the graphical user interface;

blocking a user from accepting the modified profile by making the accept area not available if the extracorporeal blood control apparatus is not able to support each of the preset therapy type and the preset therapy set of the modified profile prior to configuring the extracorporeal blood control apparatus to perform extracorporeal blood treatment according to the selected treatment profile;

displaying a rationale why the extracorporeal blood control apparatus is not able to support each of the preset therapy type and the preset therapy set of the modified profile concurrently with the preset therapy type and the preset therapy set of the modified profile; and allowing a user to select the save area to save the modified profile into the plurality of stored profiles for later use during preparation for an extracorporeal blood treatment if the extracorporeal blood control apparatus is able to support each of the preset therapy type and the preset therapy set of the modified profile.

2. The method of claim 1, wherein the plurality of different therapy types comprises at least one of SCUF, CVVH, CVVHD, CVVHDF, TPE, HP, MARS, and carbon dioxide removal.

3. The method of claim 1, wherein allowing a user to use the input apparatus to select a profile of the plurality of profiles using the profile identifier region of the graphical user interface comprises:

displaying on the graphical user interface the identifier of each of the plurality of profiles; and allowing a user to use the input apparatus to select the identifier of the selected profile.

4. The method of claim 1, wherein each profile of the plurality of profiles further comprises one or more of identification data, the identification data comprises one or more of prescribing doctor, weight, age, gender disease state, location, patient identifier, and intracellular volume, wherein the method further comprises:

displaying on the graphical user interface a profile filter region to allow a user to input identification data, allowing a user to use the input apparatus to input identification data using the profile filter region; and displaying on the graphical user interface sorted or filtered profiles of the plurality of profiles based on the input identification data.

5. The method of claim 1, wherein modifying the preset therapy type comprises:

allowing a user to use the input apparatus to select the therapy type region;

displaying a therapy type list area in the therapy type region comprising the plurality of different therapy types in response to selection of the therapy type region;

allowing a user to select a therapy type from the therapy type list area;

in response to selection of the therapy type from the therapy type list area, dismissing the therapy type list area; and displaying the selected therapy type in the therapy type region, wherein modifying the preset therapy set comprises:

allowing a user to use the input apparatus to select the therapy set region;

displaying a therapy set list area in the therapy set region comprising plurality of different therapy sets in response to selection of the therapy set region;

allowing a user to select a therapy set type from the therapy set list area;

in response to selection of the therapy set from the therapy set list area, dismissing the therapy set list area; and displaying the selected therapy set in the therapy set region.

6. The method of claim 1, further comprising allowing a user to use the input apparatus, without selecting a profile of the plurality of profiles, to select at least one of a therapy type of the plurality of different therapy types using the therapy type region of the graphical user interface and a therapy set of the plurality of different therapy sets using the therapy set region of the graphical user interface.

7. The method of claim 1, further comprising:

displaying an anticoagulation region on the graphical user interface, wherein each profile of the plurality of profiles further comprises a preset anticoagulation type of a plurality of different types of anticoagulation;

allowing a user to use the input apparatus to select a different anticoagulation type of the plurality of different types of anticoagulation than the preset anticoagulation type using the anticoagulation region of the graphical user interface;

blocking a user to proceed with accepting the modified profile if the extracorporeal blood control apparatus is not able to support each of the preset therapy type and the preset therapy set of the modified profile with the selected different anticoagulation type of the modified profile prior to configuring the extracorporeal blood control apparatus to perform extracorporeal blood treatment according to the selected treatment profile;

displaying a rationale why the extracorporeal blood control apparatus is not able to support each of the preset therapy type and the preset therapy set with the selected different anticoagulation type of the modified profile concurrently with the preset therapy type and the preset therapy set with the selected different anticoagulation type of the modified profile; and allowing a user to save the modified profile into the plurality of stored profiles if the extracorporeal blood control apparatus is able to support each of the preset therapy type and the preset therapy set of the modified profile with the selected different anticoagulation type of the modified profile.

8. The method of claim 1, wherein each profile of the plurality of profiles further comprises a preset value for at least one flow rate of a plurality of flow rates, wherein the graphical user interface is further configured to depict a flow rate region, wherein the method further comprises displaying on the graphical user interface the preset value of the at least one flow rate of the selected profile in a flow rate region.

9. The method of claim 8, further comprising:

allowing a user to use the input apparatus to adjust the preset value of the at least one flow rate of the selected profile using flow rate region; and displaying on the graphical user interface an indication proximate the adjusted preset value of the at least one flow rate of the selected profile in the flow rate region.

10. The method of claim 1, wherein each profile of the plurality of profiles further comprises at least one preset alarm value for at least one alarm limit of a plurality of alarm limits, wherein the graphical user interface is further configured to depict an alarm region, wherein the method further comprises:

displaying the at least one preset alarm value for at least one alarm limit of the selected profile in an alarm region on the graphical user interface; and allowing a user to use the input apparatus to adjust the at least one preset alarm value of the at least one alarm limit of the plurality of alarm limits of the selected profile using the alarm region of the graphical user interface.

11. The method of claim 1, wherein each profile of the plurality of profiles further comprises at least one preset anticoagulation value for at least one anticoagulation advisory of a plurality of anticoagulation advisories, wherein the graphical user interface is further configured to depict an anticoagulation advisory region, wherein the method further comprises:

displaying the at least one preset anticoagulation value for the at least one anticoagulation advisory of the plurality of anticoagulation advisories of the selected profile in an anticoagulation advisory region on the graphical user interface; and allowing a user to use the input apparatus to adjust the at least one preset anticoagulation value of at least one anticoagulation advisory of the plurality of anticoagulation advisories of the selected profile using the anticoagulation advisory region of the graphical user interface.

12. The method of claim 1, wherein the input apparatus comprises a touch screen.

13. A method for an extracorporeal blood treatment system comprising:

providing an extracorporeal blood control apparatus to perform an extracorporeal blood treatment, the extracorporeal blood control apparatus comprising one or more pumps;

providing a graphical user interface comprising a profile identifier region, a therapy type region, therapy set region, an accept area, and a save area;

providing an input apparatus configured to allow a user to create or edit a profile identifier using the profile identifier region of the graphical user interface, to select a therapy type using the therapy type region of the graphical user interface, and to select a therapy set using the therapy set region of the graphical user interface;

storing a plurality of profiles, wherein each profile of the plurality of profiles comprises an identifier, a preset therapy type of a plurality of different therapy types, and a preset therapy set of a plurality of different therapy sets, each therapy set being a replacement unit for use in performing a different therapy;

allowing a user to use the input apparatus to enter an identifier for a new profile of the plurality of profiles using the profile identifier region of the graphical user interface, to select a therapy type of the plurality of different therapy types to be the preset therapy type of the new profile using the therapy type region of the graphical user interface, and to select a therapy set of the plurality of different therapy sets to be the preset therapy set of the new profile using the therapy set region of the graphical user interface;

blocking a user to proceed with accepting the new profile if the extracorporeal blood control apparatus is not able to support each of the preset therapy type and the preset therapy set of the new profile prior to configuring the extracorporeal blood control apparatus to perform extracorporeal blood treatment according to the selected treatment profile;

displaying a rationale why the extracorporeal blood control apparatus is not able to support each of the preset therapy type and the preset therapy set of the new profile concurrently with the preset therapy type and the preset therapy set of the new profile; and allowing a user to save the new profile into the plurality of stored profiles if the extracorporeal blood control apparatus is able to support each of the preset therapy type and the preset therapy set of the new profile.

14. A method for an extracorporeal blood treatment system comprising:

providing an extracorporeal blood control apparatus to perform an extracorporeal blood treatment, the extracorporeal blood control apparatus comprising one or more pumps;

providing a graphical user interface comprising a profile identifier region, a profile selection region, a therapy type region, and a therapy set region;

providing an input apparatus configured to allow a user to create or edit a profile identifier using the profile identifier region of the graphical user interface, to select a therapy type using the therapy type region of the graphical user interface, and to select a therapy set using the therapy set region of the graphical user interface;

storing a plurality of profiles, wherein each profile of the plurality of profiles comprises an identifier, a preset therapy type of a plurality of different therapy types, and a preset therapy set of a plurality of different therapy sets, each therapy set being a replacement unit for use in performing a different therapy;

displaying the profile identifier region, the profile selection region, the therapy type region, and the therapy set region on the graphical user interface, wherein the profile selection region lists the plurality of profiles, wherein each listed profile of the plurality of profiles in the profile selection regions lists the profile identifier, the therapy type, and the therapy set;

allowing a user to use the input apparatus to select a profile of the plurality of profiles using the profile selection region of the graphical user interface;

displaying on the graphical user interface the identifier of the selected profile in the profile identifier region, the preset therapy type of the selected profile in the therapy type region, and the preset therapy set of the selected profile in the therapy set region;

allowing a user to use the input apparatus to modify one or more of the preset therapy type of the selected profile to a different therapy type of the plurality of different therapy types using the therapy type region of the graphical user interface and the preset therapy set of the selected profile to a different therapy set of the plurality of different therapy sets using the therapy set region of the graphical user interface;

blocking a user to proceed with accepting the modified profile if the extracorporeal blood control apparatus is not able to support each of the preset therapy type and the preset therapy set of the modified profile prior to configuring the extracorporeal blood control apparatus to perform extracorporeal blood treatment according to the selected treatment profile; and allowing a user to save the modified profile into the plurality of stored profiles if the extracorporeal blood control apparatus is able to support each of the preset therapy type and the preset therapy set of the modified profile.

15. The method of claim 14, wherein the plurality of different therapy types comprises one or more of SCUF, CVVH, CVVHD, CVVHDF, TPE, HP, MARS, and carbon dioxide removal.

16. The method of claim 14, wherein the graphical user interface further comprises an anticoagulation region, wherein each profile of the plurality of profiles further comprises a preset anticoagulation type of a plurality of different types of anticoagulation, wherein the method further comprises:

displaying the anticoagulation region on the graphical user interface;

allowing a user to use the input apparatus to select an anticoagulation type to be the preset anticoagulation type of the selected profile using the anticoagulation region of the graphical user interface;

blocking a user to proceed with accepting the modified profile if the extracorporeal blood control apparatus is not able to support both of the preset therapy type and the preset therapy with the selected anticoagulation type of the modified profile prior to configuring the extracorporeal blood control apparatus to perform extracorporeal blood treatment according to the selected treatment profile, and allowing a user to save the modified profile into the plurality of stored profiles if the extracorporeal blood control apparatus is able to support both of the preset therapy type and the preset therapy with the selected anticoagulation type of the modified profile.

17. The method of claim 14, further comprising allowing a user to use the input apparatus to modify the identifier of the selected profile using the profile identifier region.

18. The method of claim 14, further comprising blocking a user to proceed with saving the modified profile if one of the preset therapy type and the preset therapy set is missing.

19. The method of claim 14, wherein each profile of the plurality of profiles further comprises a preset value for at least one flow rate of a plurality of flow rates, wherein the graphical user interface is further configured to depict a flow rate region, wherein the method further comprises:

displaying the flow rate region on the graphical user interface; and allowing a user to use the input apparatus to adjust the preset value of the at least one flow rate of the selected profile using the flow rate region of the graphical user interface.

20. The method of claim 19, further comprising displaying on the graphical user interface an indication proximate the adjusted preset value of the at least one flow rate in the flow rate region.

21. The method of claim 14, wherein each profile of the plurality of profiles further comprises at least one preset alarm value for at least one alarm limit of a plurality of alarm limits, wherein the graphical user interface is further configured to depict an alarm region, wherein the method further comprises:

displaying the alarm region on the graphical user interface; and allowing a user to use the input apparatus to adjust the at least one preset alarm value of the plurality of alarm limits of the selected profile using the alarm region of the graphical user interface.

22. The method of claim 14, wherein each profile of the plurality of profiles further comprises at least one preset anticoagulation value for at least one anticoagulation advisory of a plurality of anticoagulation advisories, wherein the graphical user interface is further configured to depict an anticoagulation advisory region, wherein the method further comprises:

displaying the anticoagulation advisory region on the graphical user interface; and allowing a user to use the input apparatus to adjust the at least one preset anticoagulation value of the plurality of the plurality anticoagulation advisories of the selected profile using the anticoagulation advisory region of the graphical user interface.

23. The method of claim 14, further comprising allowing a user to use the input apparatus to transfer at least one profile of the plurality of profiles to an external device.

24. The method of claim 14, wherein the plurality of profiles comprise at least one protected profile, wherein one or more of the identifier, preset therapy type, and preset therapy set of the at least one protected profile are not modifiable by a user.

25. A method for an extracorporeal blood treatment system comprising:

providing an extracorporeal blood control apparatus to perform an extracorporeal blood treatment, the extracorporeal blood control apparatus comprising one or more pumps;

providing a graphical user interface, wherein the graphical user interface is configured to depict a profile selection interface, a profile creation/modification interface, an accept area, and a save area;

providing an input apparatus configured to allow a user to select, create, or modify one or more profiles;

storing a plurality of profiles, wherein each profile of the plurality of profiles comprises an identifier, a preset therapy type of a plurality of different therapy types, a preset therapy set of a plurality of different therapy sets, and a preset value for one or more flow rates of a plurality of flow rates, each therapy set being a replacement unit, in the form of an extracorporeal blood set, for use in performing a different therapy;

displaying on the graphical user interface the profile selection interface to allow a user to select a profile for use in a treatment;

displaying on the graphical user interface the profile creation/modification interface to allow a user to modify one or more profiles of the plurality of profiles and to allow a user to create one or more profiles to be stored in the plurality of profiles;

allowing a user to use the input apparatus to create or modify a created/modified profile of the plurality of profiles using the profile creation/modification interface of the graphical user interface comprising allowing a user to use the profile creation/modification interface to enter one or more of:

the preset therapy type of the plurality of different therapy types using the graphical user interface for the created/modified profile, the preset therapy set of the plurality of different therapy sets using the graphical user interface for the created/modified profile, and a preset value of the one or more flow rates for the created/modified profile;

blocking a user from accepting the created/modified profile by making the accept area not available if the extracorporeal blood control apparatus is not able to support each of the preset therapy type, the preset therapy set, and the preset value of the one or more flow rates of the created/modified profile prior to configuring the extracorporeal blood control apparatus to perform extracorporeal blood treatment according to the selected treatment profile;

displaying a rationale why the extracorporeal blood control apparatus is not able to support each of the preset therapy type, the preset therapy set, and the preset value of the one or more flow rates of the created/modified profile concurrently with the preset therapy type, the preset therapy set, and the preset value of the one or more flow rates of the created/modified profile; and allowing a user to select the save area to save the created/modified profile into the plurality of stored profiles for later use during preparation for an extracorporeal blood treatment if the extracorporeal blood control apparatus is able to support each of the preset therapy type, the preset therapy set, and the preset value of the one or more flow rates of the created/modified profile.

26. The method of claim 25, wherein the profile selection interface and the profile creation/modification interface are not displayed at the same time.

27. The method of claim 1, wherein the method further comprises displaying on the graphical user interface an accept area selectable by a user to accept the modified profile, wherein blocking a user to proceed with accepting the modified profile comprises not allowing the accept area to be selected by the user prior to configuring the extracorporeal blood control apparatus to perform extracorporeal blood treatment according to the selected treatment profile.

\*    \*    \*    \*    \*